United States Patent
Agee et al.

(10) Patent No.: US 6,565,563 B1
(45) Date of Patent: **\*May 20, 2003**

(54) METHOD AND APPARATUS FOR INCREASING THE RANGE OF MOTION OF ONE OR MORE CONTRACTED JOINTS THROUGH EXTERNAL FORCES INDEPENDENTLY TRANSMITTED TO THE SKELETON

(75) Inventors: John M. Agee, 3700 Toronto Rd., Cameron Park, CA (US) 95682; Jeffrey Woodhouse, Sacramento, CA (US); Francis C. King, Carmichael, CA (US)

(73) Assignee: John M. Agee, Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/571,094

(22) Filed: May 15, 2000

Related U.S. Application Data

(63) Continuation-in-part of application No. 08/935,833, filed on Sep. 23, 1997, now Pat. No. 6,063,087.
(60) Provisional application No. 60/026,956, filed on Sep. 23, 1996.

(51) Int. Cl.[7] .............................................. A61B 17/50
(52) U.S. Cl. ........................................... 606/55; 602/21
(58) Field of Search ............................... 606/54, 55, 56, 606/57, 58, 59; 602/20, 21, 22, 64

(56) References Cited

U.S. PATENT DOCUMENTS

| | | | |
|---|---|---|---|
| 4,602,620 A | 7/1986 | Marx | |
| 4,765,320 A | * 8/1988 | Lindemann et al. | 602/22 |
| 4,949,711 A | 8/1990 | Gyovai et al. | |
| 5,100,403 A | 3/1992 | Hotchkiss et al. | 606/56 |
| 5,102,411 A | 4/1992 | Hotchkiss et al. | 606/57 |
| 5,324,251 A | * 6/1994 | Watson | 602/16 |
| 5,372,597 A | 12/1994 | Hotchkiss et al. | 606/55 |
| 5,376,091 A | 12/1994 | Hotchkiss et al. | 606/56 |
| 6,063,087 A | * 5/2000 | Agee et al. | 606/55 |
| 6,093,162 A | * 7/2000 | Fairleigh et al. | 602/22 |

OTHER PUBLICATIONS

1999 Hand Therapy Catalog (selected pages) (North Coast Medical Inc., Morgan Hill, CA USA 95037–2845.
An Innovation IN PIP Fixation, BioSymMetRic Proximal Interphalangeal Joint Fixator (Biomet, Inc. advertisement).
Messina, A., M.D., Messina, J., M.D., The Continuous Elongation Treatment by the TEC Device for Severe Dupuytren's Contracture of the Fingers (Turin, Italy).
Agee, J.M., M.D., Unstable Fracture Discloations of the Proximal Interphalangeal Joint, Treatment with the Force Cople Splint.

* cited by examiner

*Primary Examiner*—Cary E. O'Connor
(74) *Attorney, Agent, or Firm*—Townsend and Townsend and Crew LLP

(57) ABSTRACT

A joint of a human upper extremity is biased by an apparatus that includes a U-shaped frame, a distal attachment portion mounted to the frame through a biasing member and attachable to the extremity at a location distal to the joint, and a wrist brace or proximal attachment portion that attaches to the extremity at a location proximal to the joint, the frame being rotatable relative to both the distal attachment portion and the wrist brace. Up to four distal attachment portions can be attached to the same U-shaped frame to bias joints on each of four distinct extremities, such as four fingers on the same hand.

48 Claims, 20 Drawing Sheets

METHOD AND APPARATUS FOR INCREASING THE RANGE OF MOTION OF ONE OR MORE CONTRACTED JOINTS THROUGH EXTERNAL FORCES INDEPENDENTLY TRANSMITTED TO THE SKELETON

RELATED APPLICATIONS

This application is a continuation-in-part of pending U.S. Application No. 08/935,833, filed Sep. 23, 1997 and entitled "METHOD AND APPARATUS FOR INCREASING THE RANGE OF MOTION OF ONE OR MORE CONTRACTED JOINTS THROUGH EXTERNAL FORCES INDEPENDENTLY APPLIED DIRECTLY TO THE SKELETON", now U.S. Pat. No. 6,063,087, which claims the benefit of U.S. Provisional Application No. 60/026,956, filed Sep. 23, 1996 and entitled "METHOD AND APPARATUS FOR INCREASING THE RANGE OF MOTION OF FINGERS SUFFERING FROM A LIMITED RANGE OF MOTION, THROUGH AN EXTERNAL FORCE TRANSMITTED TO THE SKELETON".

BACKGROUND OF THE INVENTION

1. Technical Field

The present invention relates to a medical and surgical method and apparatus for the correction of injuries and disorders of the musculoskeletal system in general and contractures of joints in particular. More particularly this invention relates to a dynamic orthopedic device designed to increase the range of motion of joints suffering from contractures particularly the small joints of the hand.

2. Related Art

Skeletal joint contractures often result from trauma, including fractures and dislocations of joints. In addition, burns and their scar contracture reduce the range of motion of joints. Contractures also result from muscle imbalance across joints secondary to diseases such as leprosy. Dupuytren's disease commonly causes flexion contractures of the small joints of the hand. However, contractures can be flexion or extension contractures and can occur in any skeletal joint.

Traditionally, these injuries have been treated with various different modalities including splinting, serial plaster casts, and surgical release. Recently, significant innovations have resulted in more effective dynamic methods of treating such injuries in certain joints. For example, U.S. Pat. No. 5,376,091 to Hotchkiss et al., incorporated herein by reference, describes a dynamic finger joint support that has a proven clinical record of successful treatment of contractures. The Hotchkiss device is designed to allow, for example, the proximal interphalangeal (PIP) joint to be flexed and extended by a continuous passive motion machine that applies torque to the joint. Such flexion and extension is known to help overcome joint contractures so that the patient is often able to regain the full range of motion in the affected joint.

A deficiency of some prior art devices, generally referred to as hand splints, is that the torque required to increase the range of motion of the joint, can only be applied to the joint through the skin overlying the skeletal segments extending from either side of the joint. In addition, the force required to increase the range of motion of a joint needs to be applied for a significant amount of time. If the force is transmitted to the skeleton indirectly through the skin, the force compromises the circulation of the skin causing it to become tender, red and inflamed. In severe cases, particularly those with compromised sensation, ulcers may develop. As shown in FIGS. 1 and 2, the Hotchkiss device 5 avoids this problem for the distal interphalangeal (DIP) joint 10 by applying force directly to both the middle phalanx 12 and the distal phalanx 14. From the top view provided by FIG. 2, it is clear that pins 16, 18, 20, 22 are embedded in the skeletal elements through the lateral surface of the middle 12 and distal 14 phalanges.

Despite the successful clinical record of devices like Hotchkiss', there is room for improvement in the field. Many of the prior art devices and methods have potential problems and significant limitations that restrict their use in many applications. In particular, as shown in FIG. 2, Hotchkiss type devices 5 are required to be mounted on the lateral surface of the bones that extend from the contracted joint 10.

The Hotchkiss type device does not appear to be useable on metacarpal phalangeal (MP) joints. In the case of the proximal interphalangeal (PIP) joint 24, for example, a Hotchkiss type device 5 appears to be most useful for the second and fifth PIP joints. However, because other fingers of the hand, including the webbing, would interfere with installation and use of the device on the middle finger and ring finger PIP joints, an alternate solution is required. Further, with regard to all of the PIP joints, there are soft tissues and tendons that glide along the lateral and medial surfaces of the phalanges, particularly the proximal phalanges of the fingers, that can be impaled by pins inserted into the sides of these phalanges, as required in Hotchkiss type devices used on the PIP joints. Additionally, installation of a Hotchkiss type device on the second and third DIP joints 10 would require the fingers to remain partially spread throughout the treatment period. The Hotchkiss device is depicted as applied to the DIP distal joint of the finger, however, this device and others including variations of the subject invention often are applied to the PIP joints of the fingers. With application of such devices to either the DIP or PIP joints, device portions mounted on the lateral and medial aspects of the finger or extending therefrom are troublesome as they impinge the adjacent fingers.

In light of such prior devices, what is needed is a means for biasing contracted joints that can be used on many different joints. What is further needed is a device that is not restricted to use only where it can be mounted on the lateral surface of the bones extending from a contracted joint. It would further be beneficial to identify a way to apply force directly to the skeleton without detrimentally disrupting soft tissue and tendons on the lateral surface of the bones extending from the joint. Such a device would preferably permit simultaneous treatment of joints of adjacent fingers.

In splinting techniques used in hand surgery and hand therapy, if a splint uses a single elastic element that crosses more than one joint to treat contracture of one or both joints, it is impossible to balance the torques applied to each of the joints. Thus, what is needed is a device or means which simultaneously applies independent, controlled torque to multiple contracted joints that are adjacent along an appendage such as a finger.

SUMMARY OF THE INVENTION

The above and other deficiencies and problems with the prior art are addressed by the present invention of a multiple contracted joint biasing apparatus and method. The inventive, apparatus crosses and selectively controls torque forces applied to each skeletal joint in axial series, specifically when a first joint is proximal or distal to another. When applied to the hand, a first adjustable joint biasing torque apparatus may be surgically attached to the dorsal surface of the middle phalanx of a finger. This first adjustable joint biasing torque apparatus may be linked to a second proximal adjustable biasing torque apparatus by a rigid linkage. The second proximal adjustable biasing torque apparatus is positioned relative to the flexion-extension axis of the proximal joint by a removable brace that extends from the forearm across the wrist to cradle or embrace the hand.

More generally, a first adjustably biased mechanical joint is positioned on the extension side of a first contracted skeletal joint. A distal member extends from the first mechanical joint and is surgically attached to the bone extending from the contracted skeletal joint. A rigid linkage extends from the first mechanical joint and is attached to a second adjustably biased mechanical joint. A proximal member extends from the second mechanical joint and is removably attached to the appendage that extends proximally from the second contracted skeletal joint.

The first adjustably biased mechanical joint is operable to rotate with the same degrees of freedom as a normal, non-contracted skeletal joint of the same type as the first contracted skeletal joint. The adjustable biasing torque is applied to the skeletal joint via the distal member in the rotational direction of the desired range of skeletal joint motion. The second mechanical joint is positioned on the exterior side of a second contracted skeletal joint which is adjacent along the appendage that extends from the first skeletal joint. The second mechanical joint is operable to rotate with the same degrees of freedom as a normal, non-contracted joint of the same type as the second contracted joint. As with the adjustable biasing torque applied to the first skeletal joint by the first mechanical joint, the adjustable biasing torque for the second mechanical joint is applied to the second skeletal joint via the proximal member in the rotational direction of the desired range of motion for the second skeletal joint.

The adjustably biased mechanical joints of the apparatus are positioned so that they do not interfere with full extension of the patient's skeletal joints. They are held in place by the attachments to the patient such that their respective biasing torques are independent of each other and their center of rotation is coincident or substantially coincident with the center of rotation of their associated skeletal joints.

The invention as applied to the MP and PIP joints of the fingers of the hand may include a wrist brace provided as a mounting point, as a means to hold the hand in position relative to the apparatus, and as a means to distribute the corrective force over a large area. In another variation, a proximal coupling plate serves as the proximal structural attachment to the hand. The wrist brace may be structurally stabilized by a fixation pin, such as a K-wire, which is attached to a bone of the hand or wrist, such as a metacarpal bone. The invention may be applied to more than one finger of the hand and up to all four finger MP and all four finger PIP joints. A "U" shaped transverse member is positioned over the dorsal surface of the brace and is pivotally attached to the distal end on the ulnar and radial sides of the brace. The ends of the "U" shaped transverse member are positioned such that a transverse line between them generally passes through the flexion and extension axes of rotation of the MP joints. In one variation, the "U" shaped transverse member may be replaced by a flexible tension element, preferably a cable or string, configured to couple the brace or proximal coupling plate with the more distal components.

Positioned dorsally above the PIP joint is an adjustably biased mechanical PIP joint. The mechanical PIP joint includes two members. The first member is an arcuate track that has an arc shaped track on its dorsal surface. The other is a slider block which engages and slides along the arcuate track member. The arcuate track member is mounted to the middle phalanx of the subject finger in such a way that the projected center of the arc is coincident or substantially coincident with the axis of rotation of the PIP Joint. Two fixation pins are drilled into the dorsal surface of the middle phalanx and the arcuate track member is secured to these pins. An adjustment means is provided to facilitate positioning the center point of the arc coincident or substantially coincident with the axis of rotation of the PIP joint.

A linkage may rigidly connect the slider block to the "U" shaped transverse member. The proximal end of this linkage may be attached to the "U" shaped transverse member through another swivel joint. The distal end of the linkage is attached to the slider block through a pin axis joint. The linkage allows the finger simultaneously to deviate in the radial and ulnar direction and to rotate through its normal range of motion during finger extension and flexion. An adjustment means is added to the length of this linkage to permit the apparatus to accommodate different hand sizes.

Thus, important aspects of the invention include a method and apparatus for applying torques to adjacent contracted joints along an appendage for the purpose of manipulating the joints to increase their range of motion. The invention incorporates the following principles:

(a) The axis of rotation of the applied torque is coincident or substantially coincident with the axis of rotation of the joint on which the torque is acting;

(b) The magnitude and direction of the torque applied to adjacent joints along an appendage can be controlled independently;

(c) The torque may be applied to the joint through a structure mounted directly to the skeleton or indirectly to the skeleton through a skin-preserving structure;

(d) The magnitude and direction of the torques applied to laterally neighboring joints, for example, joints of adjacent fingers on the same hand, can be controlled independently;

(e) The force required to leverage or counteract the torque to the most proximal joint may be applied to a brace-like structure that distributes the force over a large surface of the appendage or to proximal coupling plates which distribute forces directly to the skeleton of the hand.

An embodiment of the invention for the MP and PIP joints includes a means or device to allow the finger simultaneously to deviate in the radial and ulnar direction and to rotate through its normal range of motion during finger extension and flexion. This is achieved by connecting the part of the apparatus that is fixed to the middle phalanx of the finger to the remainder of the apparatus using a rigid linkage. The rigid linkage allows the part of the apparatus connected to the finger to move with the finger and to not restrict the movement of the finger in all of the normal planes of motion including that of MP flexion and extension where control is required.

The apparatus for this embodiment of the invention includes a force generating member such as a torsion spring, elastic band, servo-electrical, servo-hydraulic, coil compression or extension spring or the like; an apparatus that has a rotational movement where the axis of rotation of the device can be placed coincident or substantially coincident with the axis of rotation of a particular finger joint; and a means for attaching the force generating member to the apparatus that has a rotational movement such that the force is converted into a torque that acts about the center of rotation of the rotational apparatus.

Without the force generating members attached, the skeletal joints remain free to flex or extend and the fingers are free to deviate from side to side at MP joint level. If a force generating member is attached to only one of the mechanical joints of the apparatus, the other mechanical joint of the apparatus remains free to flex or extend without application of a biasing load. Thus, the mechanical joints of the apparatus are truly independent of each other and the torque generated by one mechanical joint of the apparatus is truly independent of any torque produced by the other.

BRIEF DESCRIPTION OF THE DRAWINGS

The features and advantages of the present invention will be understood upon consideration of the following detailed description of the invention in light of the accompanying drawings of which.

DETAILED DESCRIPTION OF THE PREFERRED EMBODIMENTS

The principles of the present invention are applicable to rehabilitate any set of contracted joints that are adjacent along a given appendage. For example, the present invention can be applied to simultaneously provide independent biasing torques to the PIP and MP joints. In addition, the present invention can be used to independently and simultaneously bias any combination of the joints in the first through fifth fingers. As a specific example of a preferred embodiment, the present invention is described herein as it would be applied to provide simultaneous yet independent biasing torques to the third (ring) finger PIP and MP joints of the left hand. However, the present invention may be adapted to accommodate other jointed appendages of the body, such as the foot for example.

Figure 3:
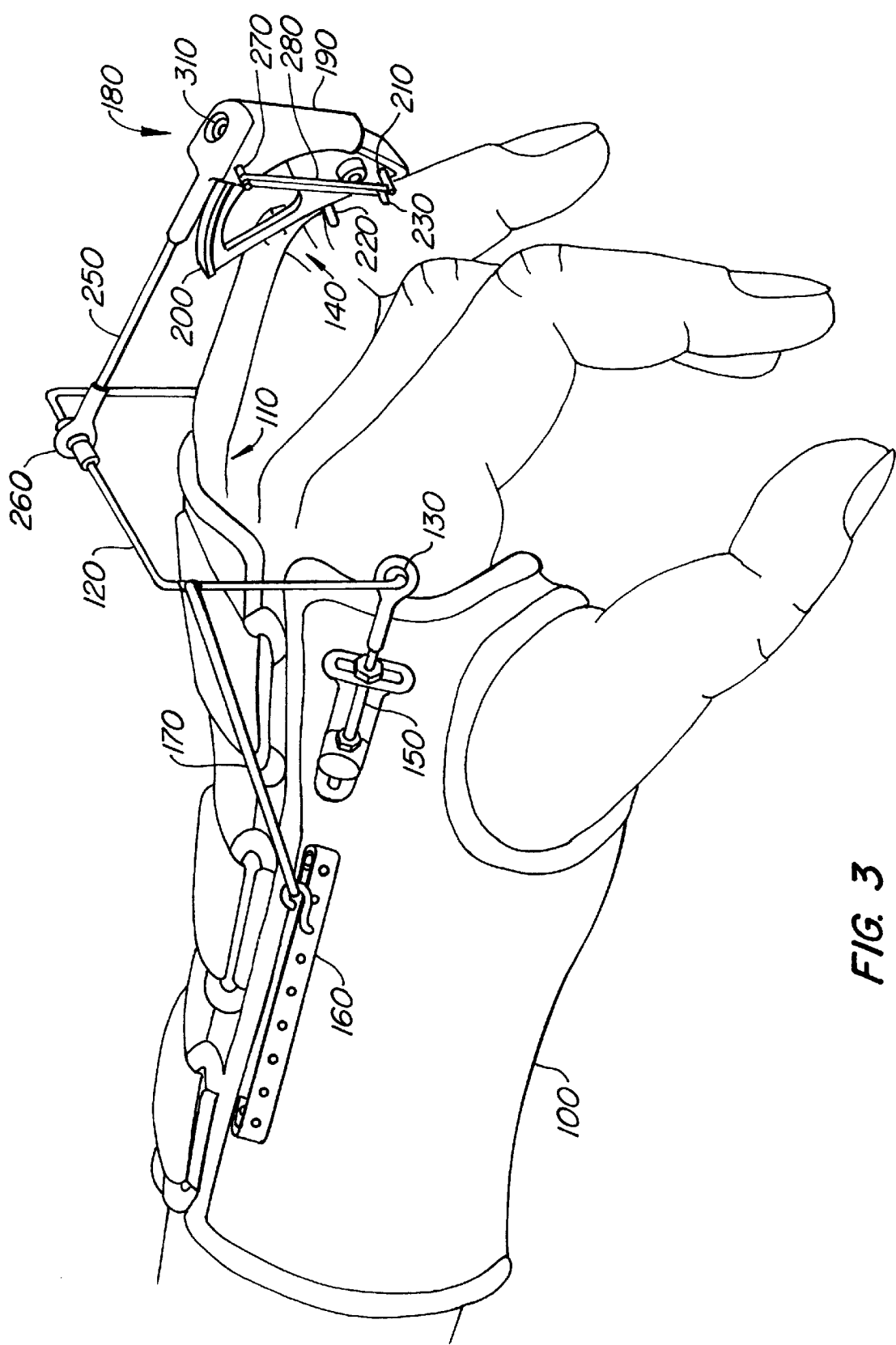
FIG. 3 is a perspective view depicting an embodiment of the present invention for the MP and PIP joints.

An exemplary embodiment of the invention is depicted in FIG. 3. A wrist brace 100 serves as a preferred means of attaching the proximal end of the apparatus to the patient. A commercially available brace such as model number 317085 available from Royce Medical Products of Camarillo, Calif. can be modified to include mounting points for the apparatus. The use of a wrist brace 100 provides the benefit of holding the hand in a desired position relative to the apparatus and it allows the biasing torque that is applied to the third MP joint 110 to be distributed over a large area. This avoids blanching of the skin when the torque is applied. Alternatively, a pair of pins surgically embedded in the index finger metacarpal bone or other suitable metacarpal bone could be used to support the apparatus at the proximal end if necessary. This alternative would be required for example, in order to apply the invention to the first (thumb) MP and IP joints, or to a hand which has been burned and cannot tolerate a skin contact brace.

Figure 10:
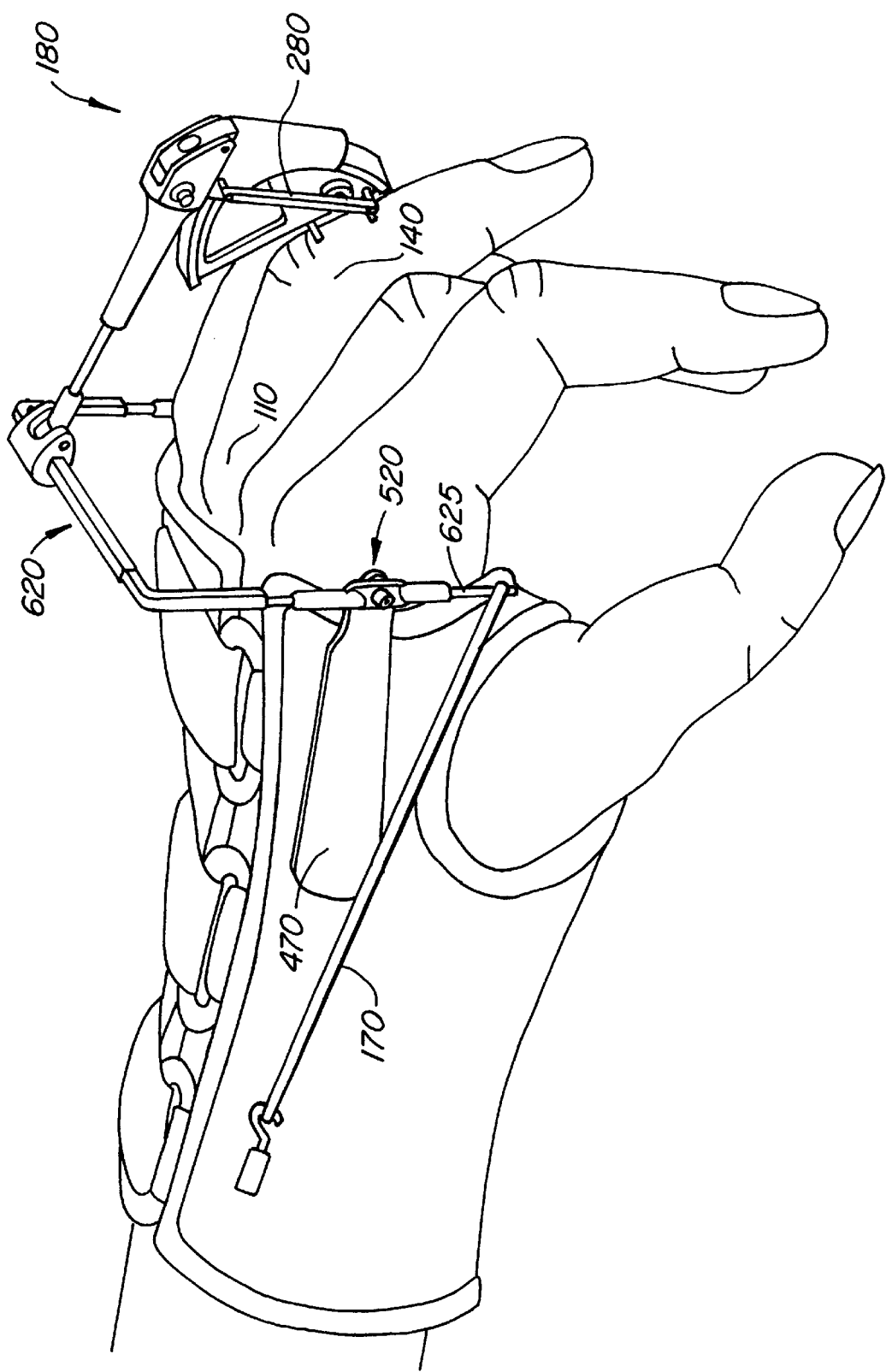
FIG. 10 is a perspective view depicting a variation of the present invention having a U-shaped member configured to facilitate flexion biasing of at least one MP joint of the hand.

Positioned over the dorsal surface of the wrist brace 100 is a "U" shaped transverse member 120 that is attached to the wrist brace 100 through two swivel joints 130 on the ulnar and radial sides of the wrist brace 100. The swivel joints 130 are positioned such that a line drawn between their centers would generally pass through the axes of rotation of the MP joints of the hand. The "U" shaped transverse member 120 is a formed piece of wire of suitable diameter and strength to maintain its shape. In an alternative embodiment, the "U" shaped transverse member 120 can include extensions (not pictured) that extend in a palmar direction beyond the swivel joints 130, as is depicted in FIG. 10. Such extensions would provide alternative locations for attaching a tension element 170 to apply a torque to the MP joint in the flexion direction.

In the example embodiment of the invention depicted in FIG. 3, the swivel joints 130 are ball and socket joints and are adjustably attached to the wrist brace 100 to facilitate lining up the swivel joints 130 with the axes of the MP joints. As shown FIG. 3, the ball and socket joints (or any other suitable pivot means) include an extension 150 that allows the center of the joint to be located adjacent to the MP joints. The extension 150 can include a length adjustment or alternatively, Velcro can be used to attach the swivel joints 130 to the wrist brace 100 at the desired location. The wrist brace 100 also includes an adjustable tension mount 160 for attaching a tension element 170 between the wrist brace 100 and the "U" shaped transverse member 120 to extend the MP joint.

Positioned dorsally above the third PIP joint 140 is a mechanical PIP assist joint 180. The mechanical PIP assist joint 180 is comprised of two slidably engaged members: a slider block 190 and an arcuate track member 200. The arcuate track member 200 includes an arc shaped track on its dorsal surface and is mounted on the middle phalanx of the subject finger in such a way that the projected center of the arc would be coincident or substantially coincident with the axis of rotation of the PIP Joint. The slider block 190 engages and slides along the arcuate track member 200. The arc shaped track terminates with stop pins (not pictured) that prevent the slider block 190 from disengaging from the arcuate track member 200 at the ends.

Figure 4:
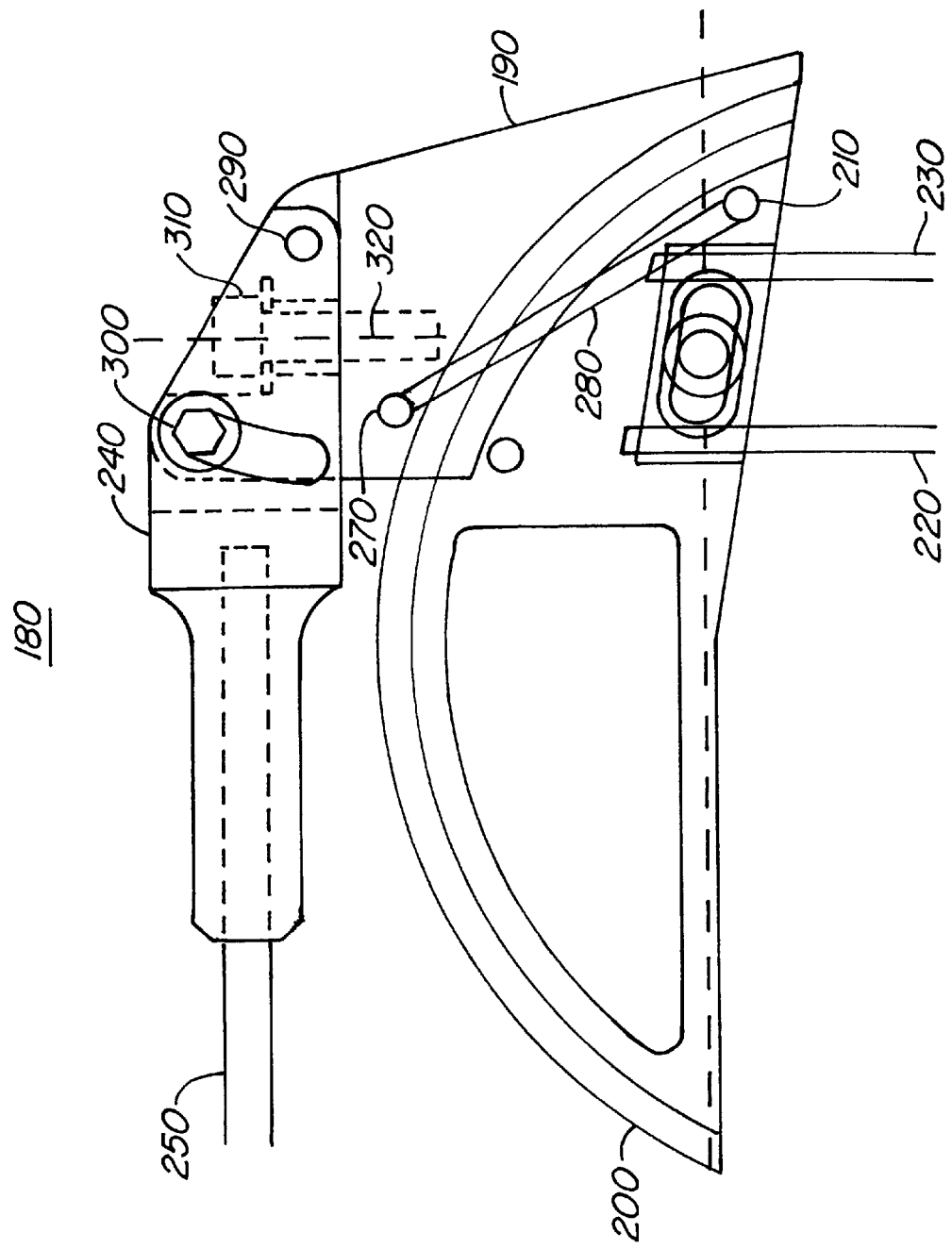
FIG. 4 is a side detail view of the PIP joint portion of the embodiment of the present invention depicted in FIG. 3.

Referring to FIG. 4, a detailed view of the mechanical PIP assist joint 180 is depicted. The angle of arc of the arcuate track member 200 is set based on the normal unimpaired range of the subject joint. In the case of the PIP joint 140, the preferred angle of the arc of the arcuate track member 200 is approximately 190 degrees. This angle supports a full range of motion for this joint without allowing the apparatus to impinge upon the finger. In the preferred embodiment of the invention, two 'K' wires, fixation pins, or screws 220, 230 extend from the arcuate track member 200 as shown in FIG. 4. These pins 220, 230 are surgically drilled through the dorsal cortex of the middle phalanx and extend into the palmar cortex of the middle phalanx. The pins 220, 230 should not extend beyond the palmar cortex surface to avoid injury to the flexor tendons. The arcuate track member 200 is adjustably secured to these pins 220, 230. The adjustments are provided to facilitate positioning the center of the arc of the arcuate track member 200 coincident or substantially coincident with the axis of rotation of the PIP joint.

An arc tension mounting pin 210 extends out from one of the lateral surfaces of the arcuate track member 200 and a corresponding slider tension mounting pin 270 extends out from one of the lateral surfaces of the slider block 190. In FIG. 4, the arc tension mounting pin 210 is located near the distal end of the arcuate track member 200. This allows the apparatus to exert an extension torque upon the PIP joint. Alternatively, the arc tension mounting pin 210 can be located on the lateral surface near the proximal end of the arcuate track member 200. This placement (not shown) of the arc tension mounting pin 210 would allow the mechanical PIP assist joint 180 to apply a flexion biasing torque to the PIP joint.

Referring back to FIG. 3, connecting the slider block 190 to the "U" shaped transverse member 120 is a rigid linkage 250. The proximal end of this rigid linkage 250 is attached to the "U" shaped transverse member 120 through a swivel joint 260. Referring back to FIG. 4, the distal end of the linkage 250 is attached to the slider block 190 through an adjustable linkage connector 240. The connector 240 is pivotally received on the upper surface of slider block 190. That is, connector 240 can rotate about bolt 310, which defines a pivot axis 320, relative to slider block 190. This linkage connector 240 includes an angle adjustment that allows the angle between the rigid linkage 250 and the slider block 190 to be adjusted to fit different sized hands. The angle adjustment can be comprised of a pin pivot hinge 290 and a locking set screw 300 or any functionally equivalent angle adjustment means.

Returning to FIG. 3, the swivel joint 260 coupling the linkage 250 to the "U" shaped transverse member 120 allows the subject finger to deviate in the radial and ulnar directions and to rotate through its normal range of motion during finger extension and flexion. Note that each increment of radial and ulnar deviation of the finger has an obligate degree of longitudinal rotation of the finger. Therefore, the linkage 250, with its pivot and swivel couplings, simultaneously permits rotation of the finger about its longitudinal axis, as well as the rotations of flexion and extension of the finger about its MP joint. An adjustment to the length of this rigid linkage 250 permits the invention to accommodate different hand sizes or to allow adjustment of the position of the slider block 190 relative to the arcuate track member 200.

With this embodiment of the invention, both the PIP 140 and MP 110 joints are free to move through their full range of motion with no external force being applied. When the PIP joint 140 is flexed or extended the arcuate track member 200 is rotated around the axis of the joint and the slider block 190 travels along the arcuate track member 200. When the MP joint 110 is flexed or extended the arcuate track member 200 and the slider block 190 remain in the same position relative to each other. Motion of the MP joint 110 is transmitted through the arcuate track member 200 and slider block 190 via the linkage 250 to the "U" shape transverse member 120 which rotates on its swivel joints 130.

To treat a finger with a limited range of motion due to MP and/or PIP joint contractures, independent external forces can be applied to the skeleton using this embodiment of the invention such that the stiff joints will be subjected to a constant, substantially constant, or controllable torque, which typically modifies the soft tissues of the joint, and thereby increases the range of motion in the desired direction. In the case of the PIP joint 140, the desired biasing torque is generated by a tension element 280 applied between the arcuate track member 200 and the slider block 190.

The tension element 280 (or "motor") can include tension springs (either extension or compression) or elastic bands, for example, and can be applied so that the torque applied to the contracted joint 140 will tend to increase the flexion or increase the extension of the subject joint 140. In the case of the MP joint 110, the tension element 170 is applied between the wrist brace 100 and the 'U' shaped transverse member 120. As with the PIP joint 140, an elastic band or either a compression or extension spring can be used to increase the flexion or extension of the MP joint 110. The amount of biasing torque applied to the joints can be controlled by changing the "strength" of the tension elements 170, 280. The biasing torque may also be changed by shifting the location of attachment of the tension element 170 on the 'U' shaped transverse member 120 such that it moves closer to pivot 130, thereby decreasing the leverage of the tension element 170 and therefore decreasing the extension torque on the MP joints of the fingers. In addition, the direction of the torque can be reversed by connecting the tension element 170 to the previously described palmar extensions of element 120, at a location palmar to pivot axis 130. The direction of the torque applied to the PIP joint can likewise be reversed by locating the mounting pin 210 (and its associated tension element 280) on the arcuate track 200 near the proximal end of the arcuate track 200.

In an alternative embodiment, the tension elements 170, 280 can be a rigid (non-elastic) adjustable length member. For example, a turnbuckle type device can be used to set a rigid tension element to any desired position. Another example of a rigid adjustable length member would include a worm screw driving mechanism with a releasable clutch, such as disclosed in the Hotchkiss patent, to set a desired length of the adjustable length member. This alternative embodiment would work to expand the joint's range of motion based on a stress/relaxation principle as opposed to the constant or relatively constant torque of the preferred embodiment. The rigid adjustable length member is set to torque against the joint's contracture for a period of time and once the joint relaxes, the length is reset to once again torque the joint. This resetting procedure is repeated until the full or maximum range of motion is restored to the joint.

In a situation where more than one finger on the same hand would benefit from an increased range of motion, additional arcuate track members 200 and slider blocks 190 could be attached to the additional fingers and connected to the "U" shaped transverse member 120. In this embodiment, the torque applied to each of the PIP joints can adjusted independently of each other. To allow the application of different biasing torques to the MP joints, additional "U" shaped transverse members within the existing "U" shaped transverse member 120 would be required. Alternatively, pins embedded in the metacarpal bones could be used to anchor the proximal end of the apparatus.

An essential feature of the invention is that the movement of the subject appendage is not restricted by the apparatus and the patient is not prevented from using the appendage during treatment. Further, in the embodiment described above, only two surgically installed pins are required to treat the PIP and MP joints.

In addition, the biasing torque generated and applied to each joint is independent of the torque generated and applied to the other joints, with the exception of a scenario wherein multiple PIP joints are biased simultaneously; in such a situation, the MP joints generally must then be biased in the same direction—either in flexion together, or in extension together—unless a multiple "U" shaped member construct is utilized. This allows treatment of the different joints with different biasing torques as required when treating multiple contracted joints. In other words, in the embodiment described above wherein one PIP joint is biased, moving either the PIP or MP joint through its complete range of motion has no functional effect on the other joint. This independent action results from the axes of rotation of the torque generating elements being coincident or substantially coincident with their respective skeletal joint axes.

Figure 5A:
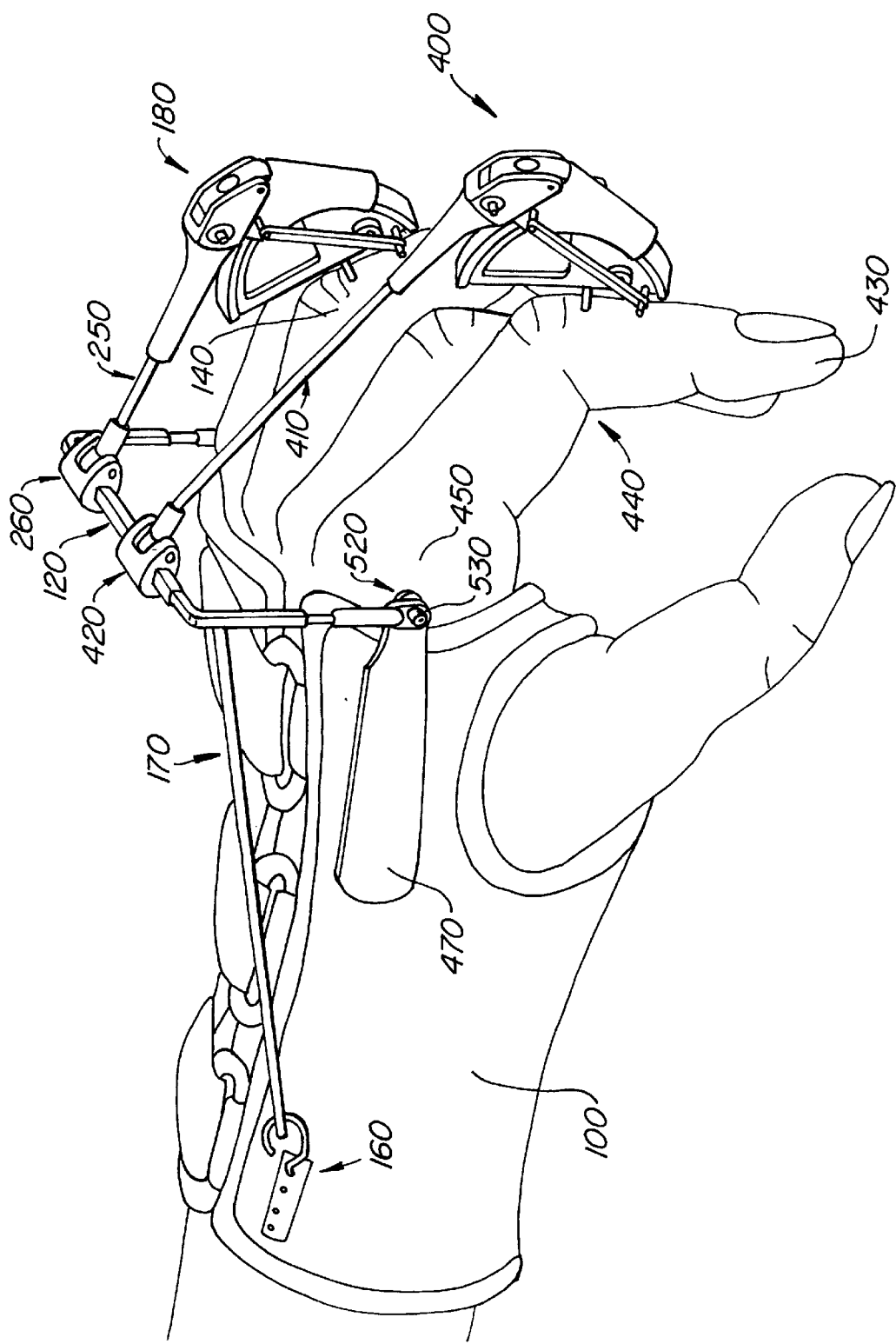
FIG. 5A is a perspective view depicting a variation of the present invention configured to bias multiple fingers of the same extremity.
Figure 5B:
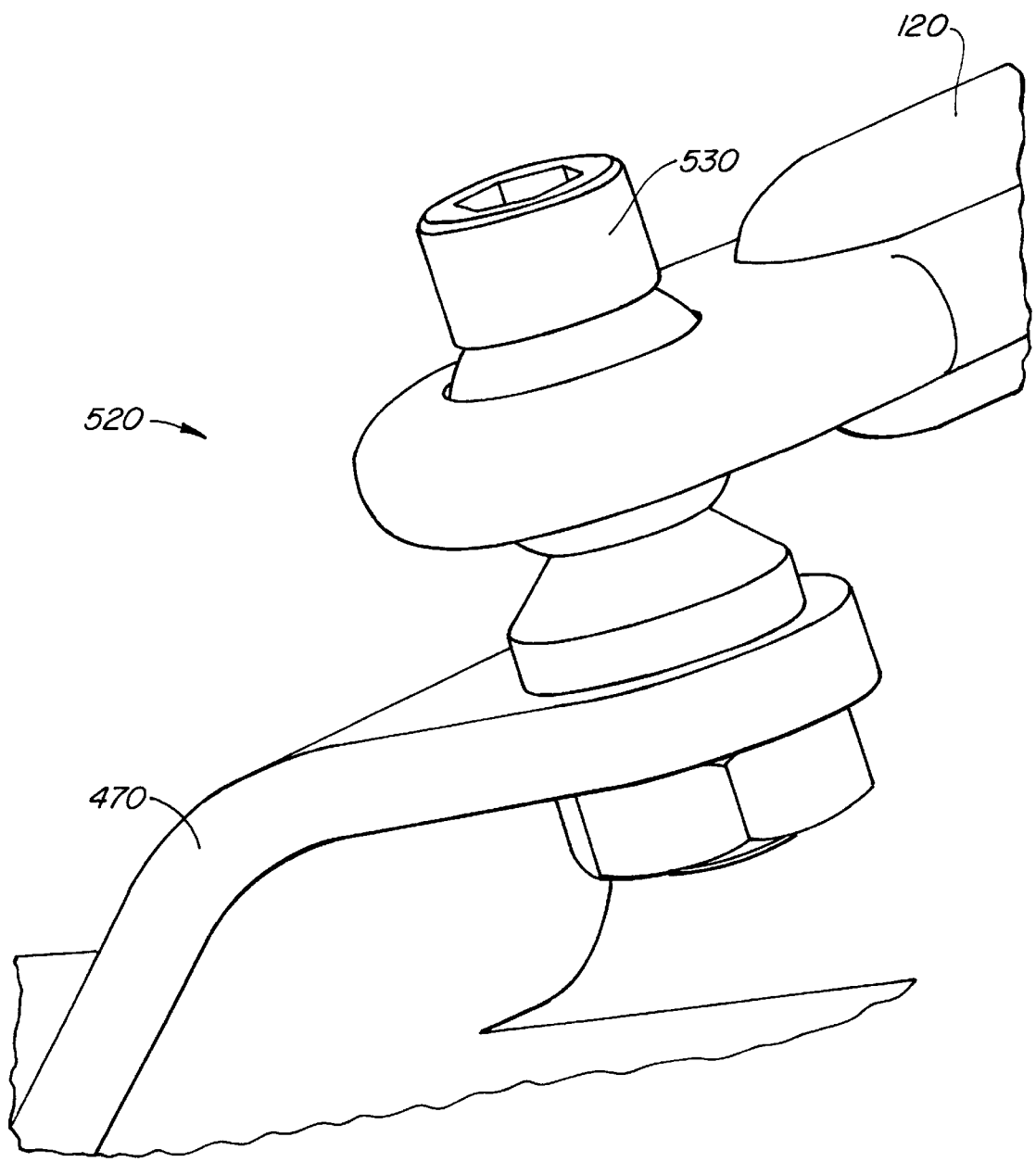
FIG. 5B is a close-up perspective view depicting a variation of a ball and socket rotatable coupling which may be used in the present invention.

Referring to FIG. 5A, a variation of the invention configured for biasing the multiple joints of multiple fingers is depicted. While two mechanical PIP assist joint constructs 180 are depicted in the figure for clarity, up to four may be coupled to the "U" shaped transverse member 120. The PIP joints 440 of the fingers may be biased independently due to the separately functioning mechanical PIP assist joints 180, 400. Thus, while the PIP joint of one finger may be biased in flexion and the PIP joint of another finger biased in extension, simultaneously, the MP joints of the fingers of the same hand are biased together in the same direction. The MP joints 450 are biased together through the "U" shaped member and its associated tension element or biasing member 170 and tension mount 160. As shown in the figure, the second mechanical joint 400, which is secured to the middle phalanx of the second finger 430, is coupled to the "U" shaped transverse member through a second rigid linkage 410 using a swivel joint 420 which sits adjacent the first swivel joint 260. In this variation, the "U" shaped transverse member 120 is rotatably coupled with the wrist brace 100, using a substantially flat coupling plate 470 which is preferably fastened to the brace 100 using an easily repositionable material such as Velcro. The "U" shaped transverse member is coupled with the coupling plate 470 by a ball and socket joint 520 comprising a specialized ball and socket pin 530 in this variation. Referring to FIG. 5B, this ball and socket joint 520 is depicted in greater detail. The ball and socket joint 520 is formed using the specialized ball and socket pin 530, which also functions as a fastener to couple the coupling plate with the "U" shaped transverse structural member 120. The action of the ball and socket joint allows the device to rotate without the requirement that the coupling plate 470 be positioned in a particular plane, as would be the case with a more restrictive pinned joint. The ball and socket joint 520 also accommodates slight rotation of the fingers about their longitudinal axes as they deviate side to side in some hand motions.

Figure 6A:
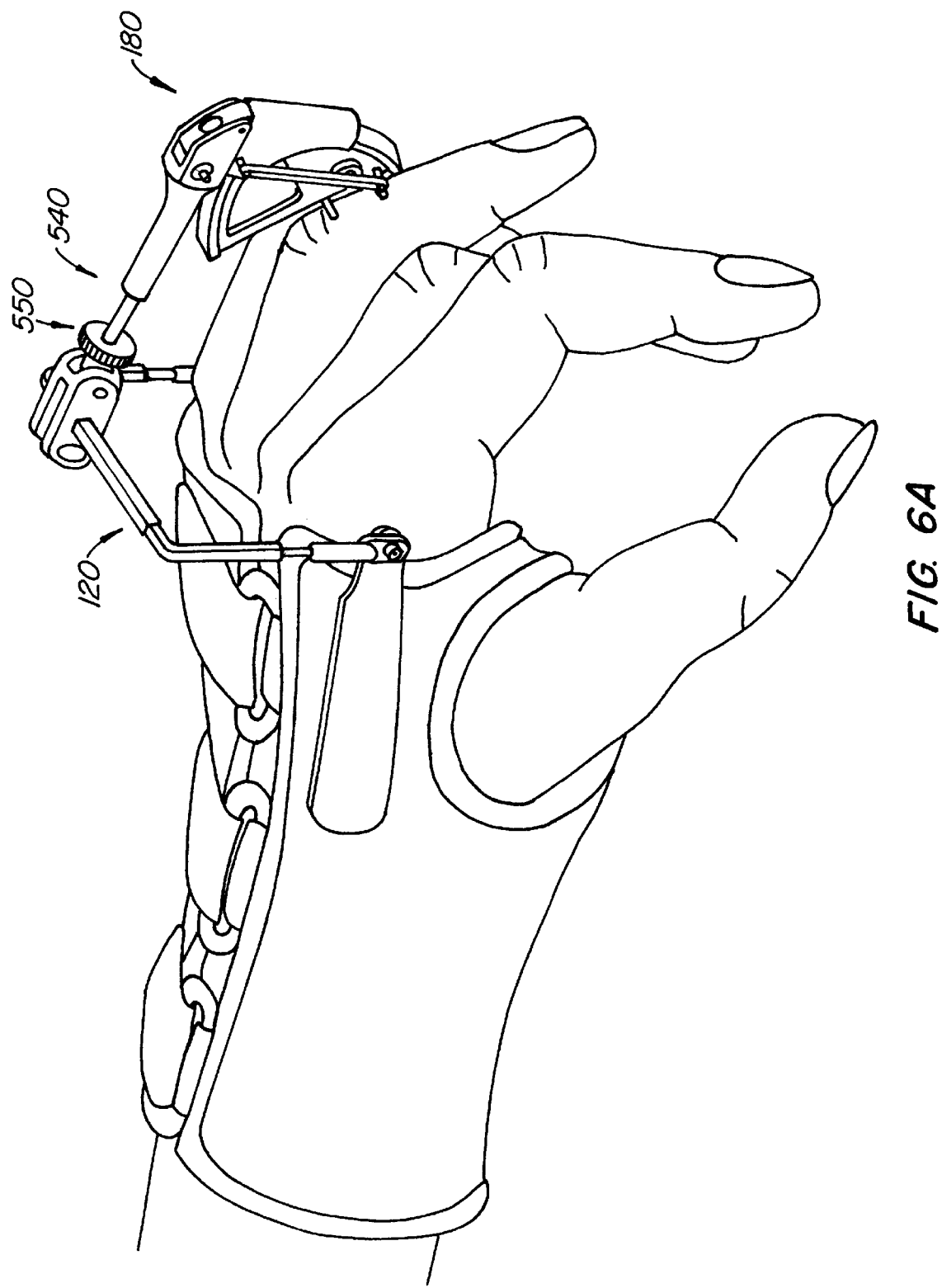
FIG. 6A is a perspective view depicting a variation of the present invention having an easily adjustable structural member.
Figure 6B:
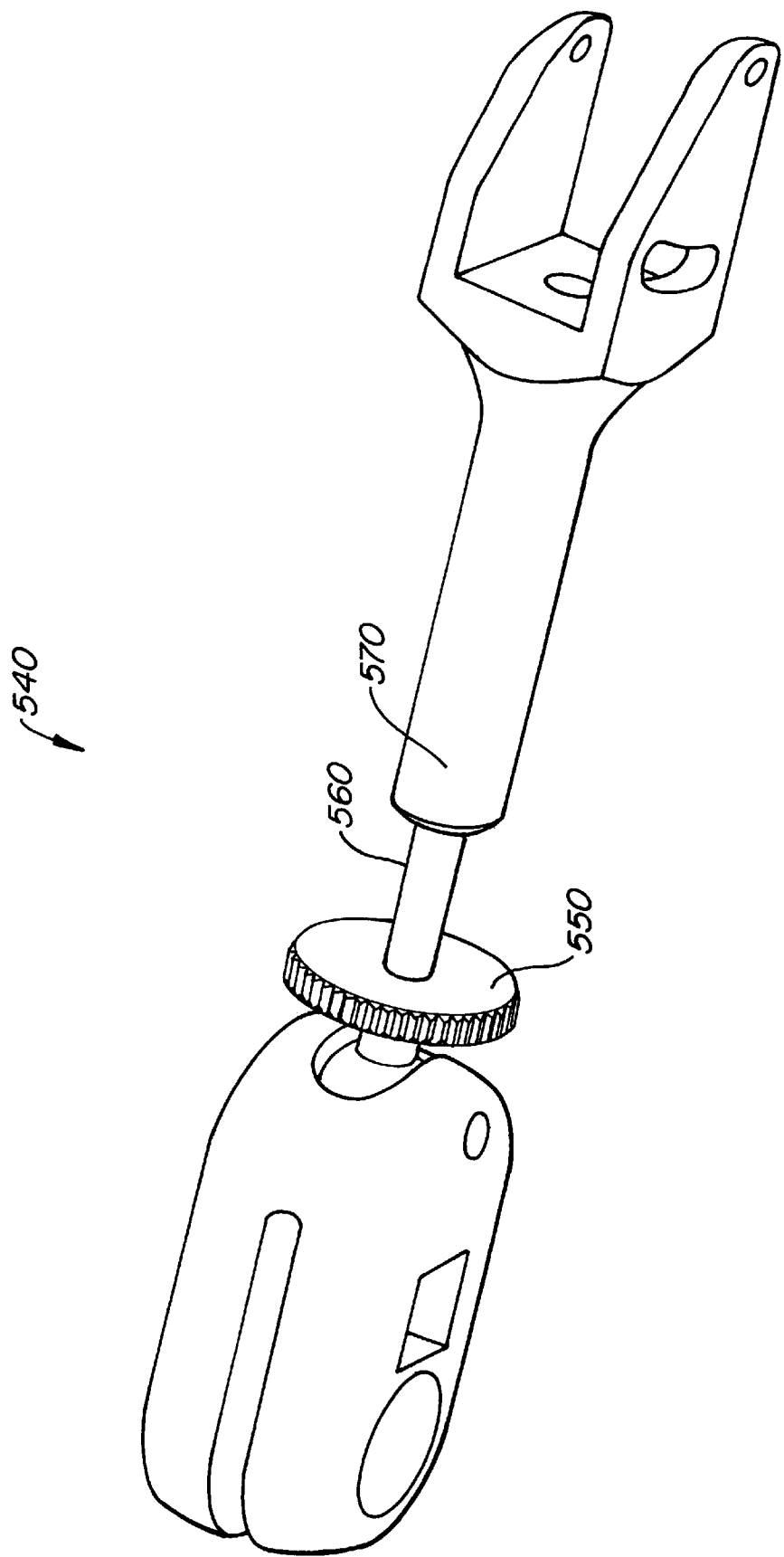
FIG. 6B is a close-up perspective view of the easily adjustable structural member of FIG. 6A.

Referring to FIG. 6A, a variation similar to that shown in FIG. 5A is depicted. This variation has an easily adjustable structural member 540 which may be changed in length by turning the associated wheel 550. Turning the wheel 550 changes the relative distance between the mechanical PIP assist joint 180 and the "U" shaped transverse structural member. Referring to FIG. 6B, this adjustable structural member 540 is shown in further detail. When the wheel 550 is turned, the threaded shaft 560 to which it is coupled turns within the proximal end of the threaded distal portion 570, thus producing relative motion and a lengthening or shortening of the adjustable structural member construct 540.

Figure 7A:
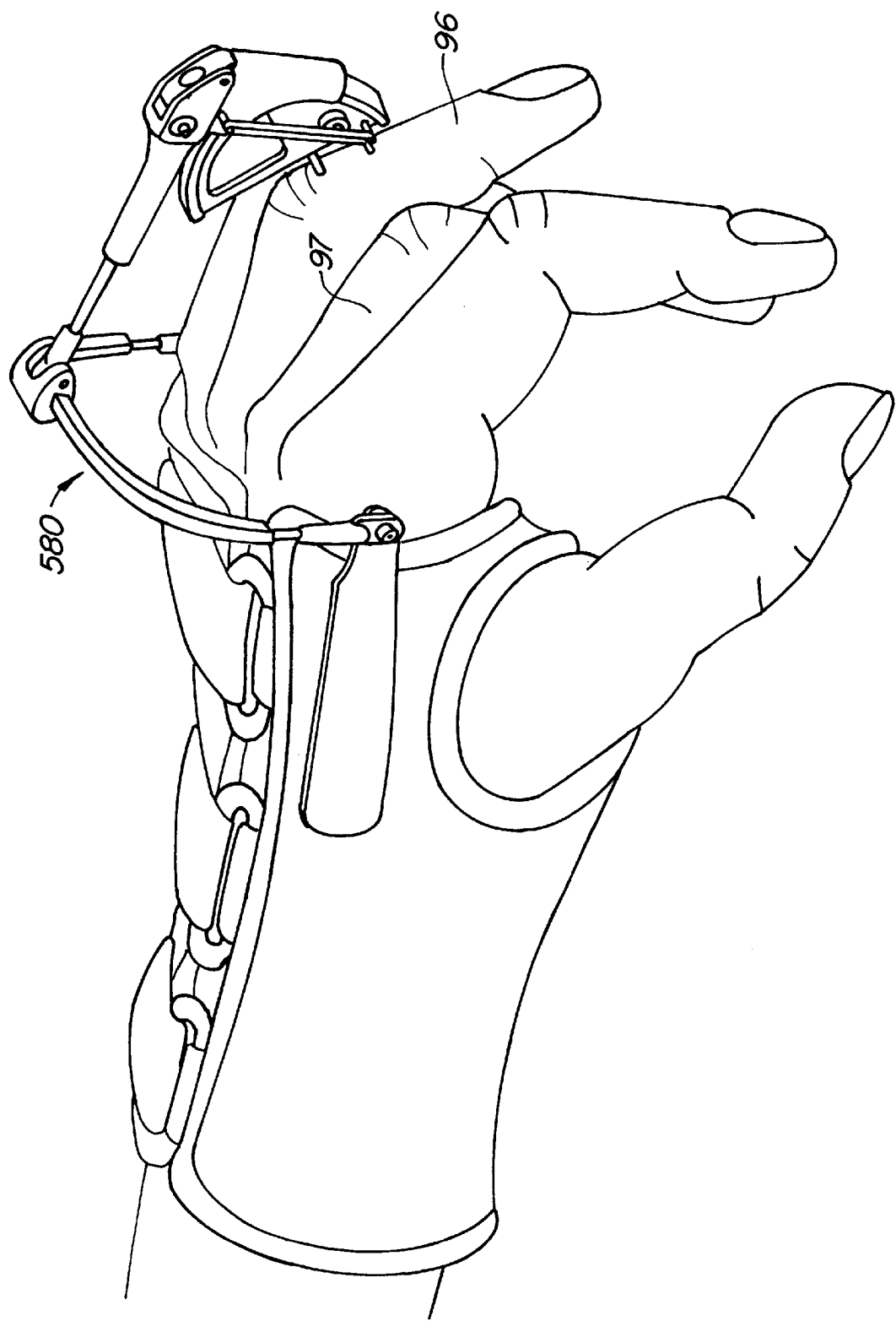
FIG. 7A is a perspective view depicting a variation of the present invention having an arcuate U-shaped member.
Figure 7B:
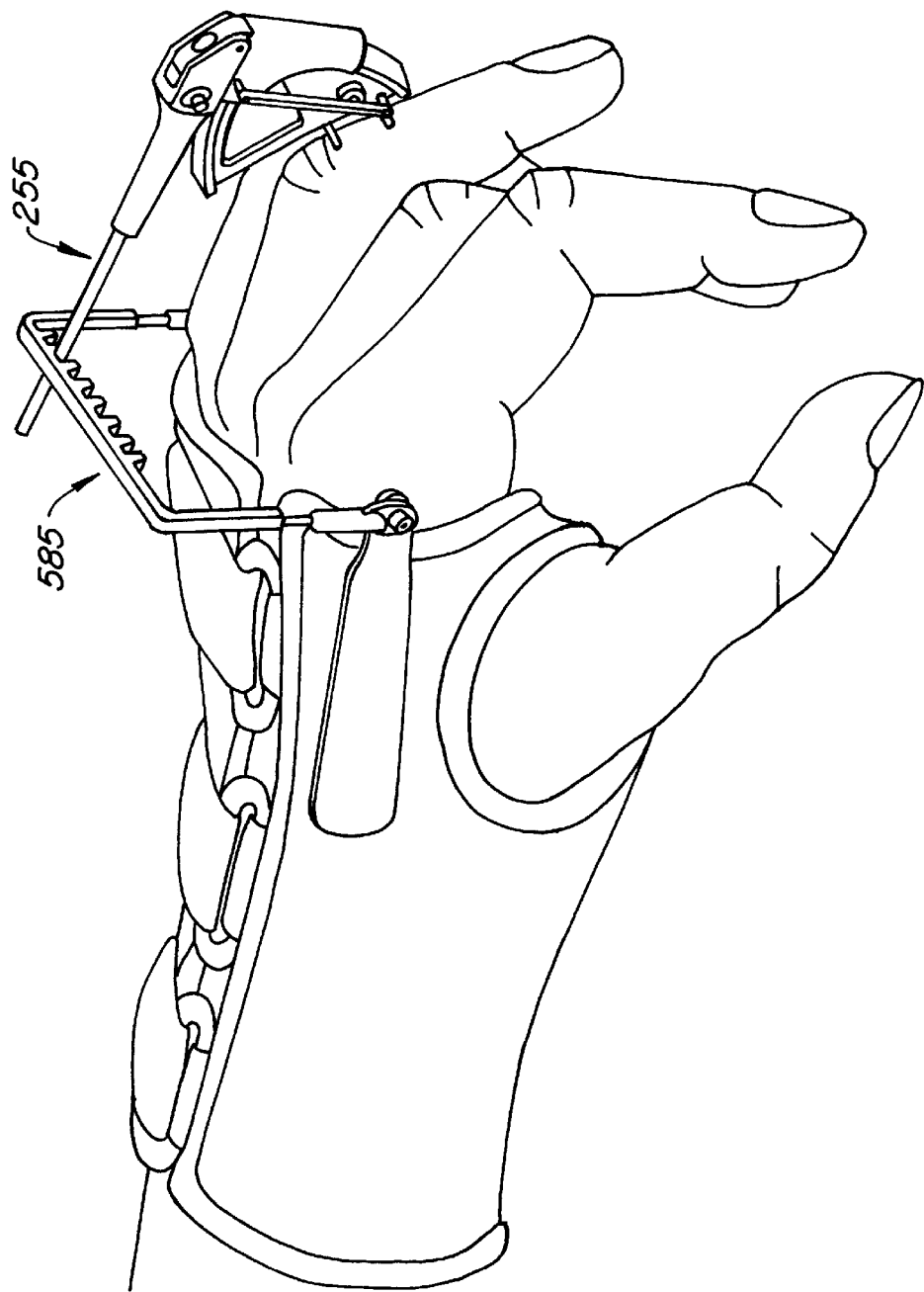
FIG. 7B is a perspective view depicting a variation of the present invention having a slotted U-shaped member.

Referring to FIG. 7A, a variation of the inventive device is shown having an arcuate "U" shaped transverse structural member 580. The arcuate shape is best used in scenarios where one of the ring 96 or middle 97 fingers is to be biased and where a transverse structural member with a lower geometric profile is helpful. FIG. 7B depicts another variation of the inventive device having a slotted "U" shaped member 585 which is configured to interface with a rigid member 255 having an unattached proximal end. This variation is configured to function similarly to those depicted in FIGS. 6A and 7A, with the exception that the overall construct is less constrained due to the lack of structural affixation between the rigid member 255 and the slotted "U" shaped member 585.

Figure 8:
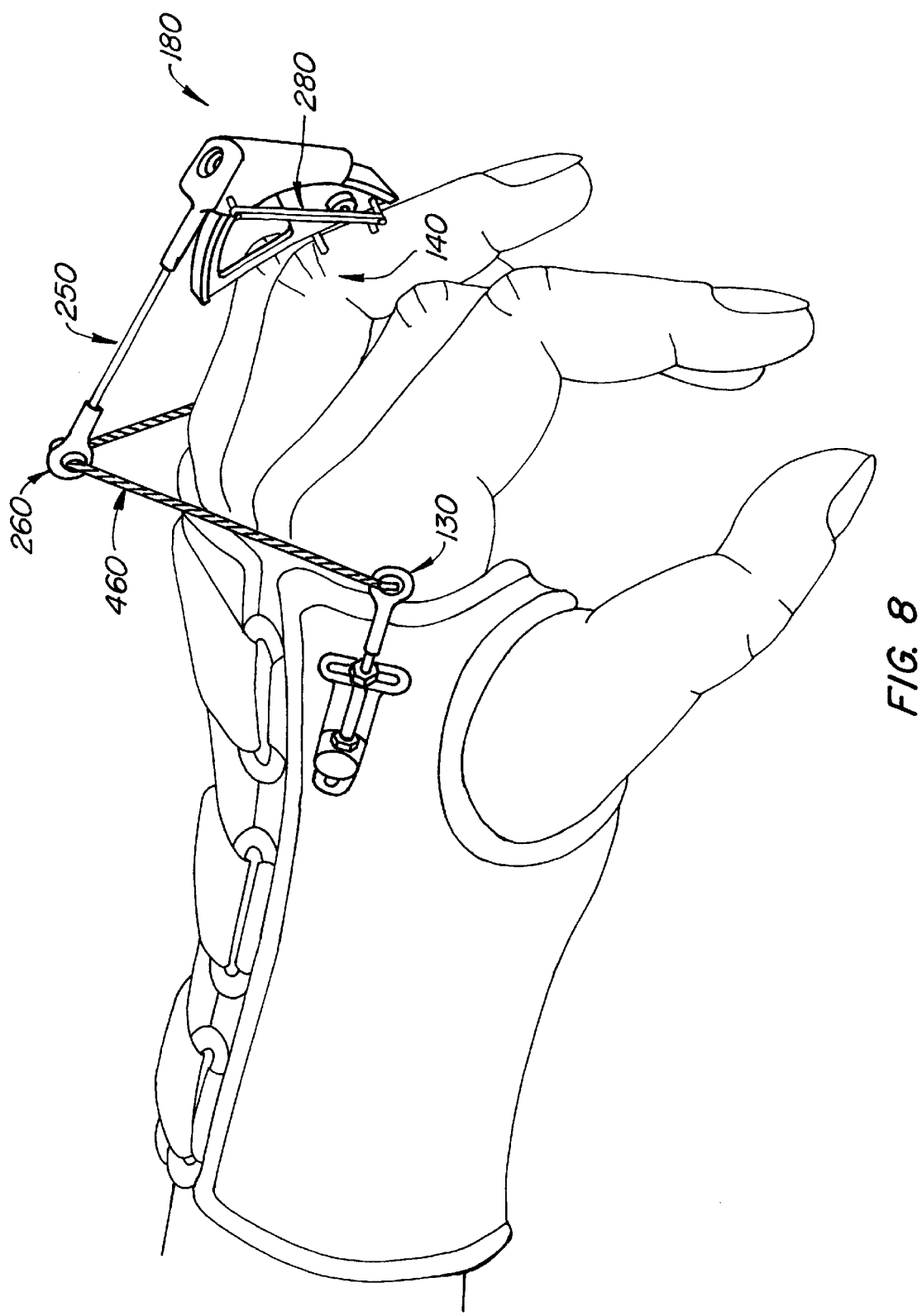
FIG. 8 is a perspective view depicting a variation of the present invention having a flexible tension element.

Referring to FIG. 8, a variation of the invention having a flexible tension element 460 in place of the "U" shaped member of other variations is depicted. The flexible tension element, preferably a cable or string, is coupled to the two swivel joints 130 of the wrist brace and passes through the swivel joint which comprises the rigid linkage 250 coupled to the mechanical PIP assist joint construct 180. The flexible tension element 460 limits the rotation of the rigid linkage 250, thereby providing a mechanism for applying a moment to the more distally located PIP joint 140 using a tension element 280. This variation is designed for use when the mechanical assist joint 180 is configured to extend the PIP joint 140 using tension in the tension element 280, as shown in FIG. 8. If the tension element 280 were configured to actually apply an extension load, a rigid "U" shaped transverse structural member would instead be preferred, as shown, for example, in FIG. 5A.

Figure 9:
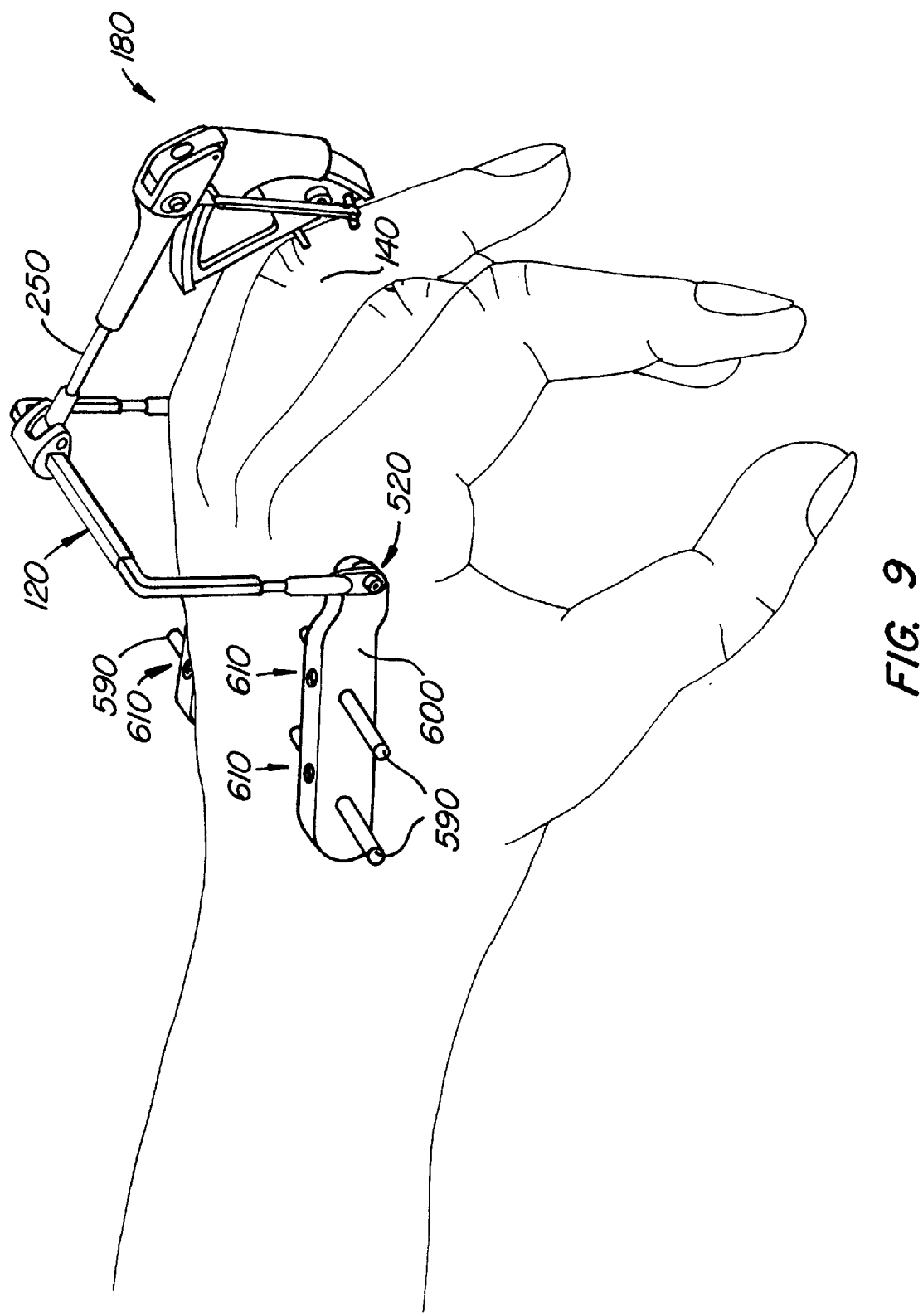
FIG. 9 is a perspective view depicting a variation of the present invention having proximal coupling plates configured to mount directly to the skeleton of the hand.

Referring to FIG. 9, a variation of the invention is depicted for applying a biasing load to a PIP joint 140 using a mechanical assist joint 180 coupled to a "U" shaped transverse structural member 120 using a rigid linkage 250. The "U" shaped transverse structural member 120 is rotatably coupled to a proximal coupling plate 600 using a ball and socket joint 520. The proximal coupling plate 600 is fastened directly to the skeleton of the hand, preferably to the metacarpal bone of the index finger and the metacarpal bone of the smallest finger, as shown in FIG. 9, using pins 590. Relative motion between the pins 590 and the proximal coupling plate 600 is prevented using set screws 610 which are fastened after the coupling plate 600 and pins 610 are in a desired position.

Referring to FIG. 10, a variation of the invention is depicted in a configuration for applying an MP flexion moment using a tension element 170 which is coupled to a "U" shaped transverse structural member 620 having an MP flexion portion 625 which extends below the ball and socket joint 520 at which "U" shaped member 620 is coupled with the coupling plate 470. This variation demonstrates that a PIP joint may be biased in extension using a mechanical biasing joint 180 with a tension element 280, while an MP joint 110 is independently biased in flexion.

Figure 1:
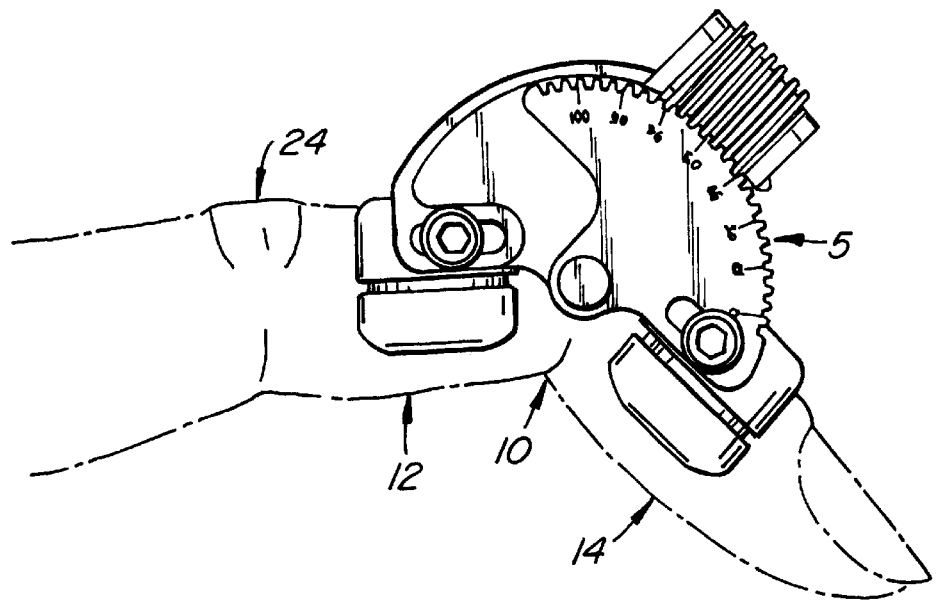
FIG. 1 is a side view depicting a dynamic DIP joint support of the prior art.
Figure 2:
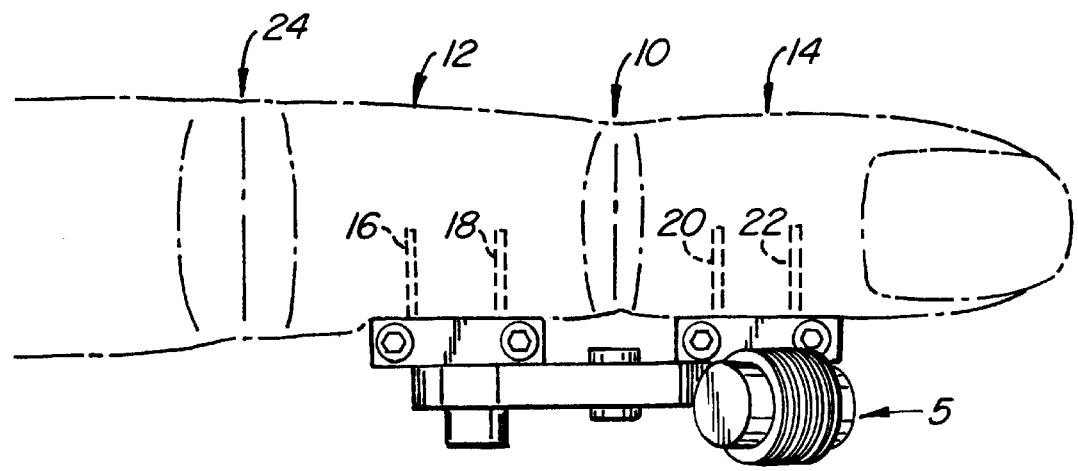
FIG. 2 is a top view depicting a dynamic DIP joint support of the prior art.
Figure 11A:
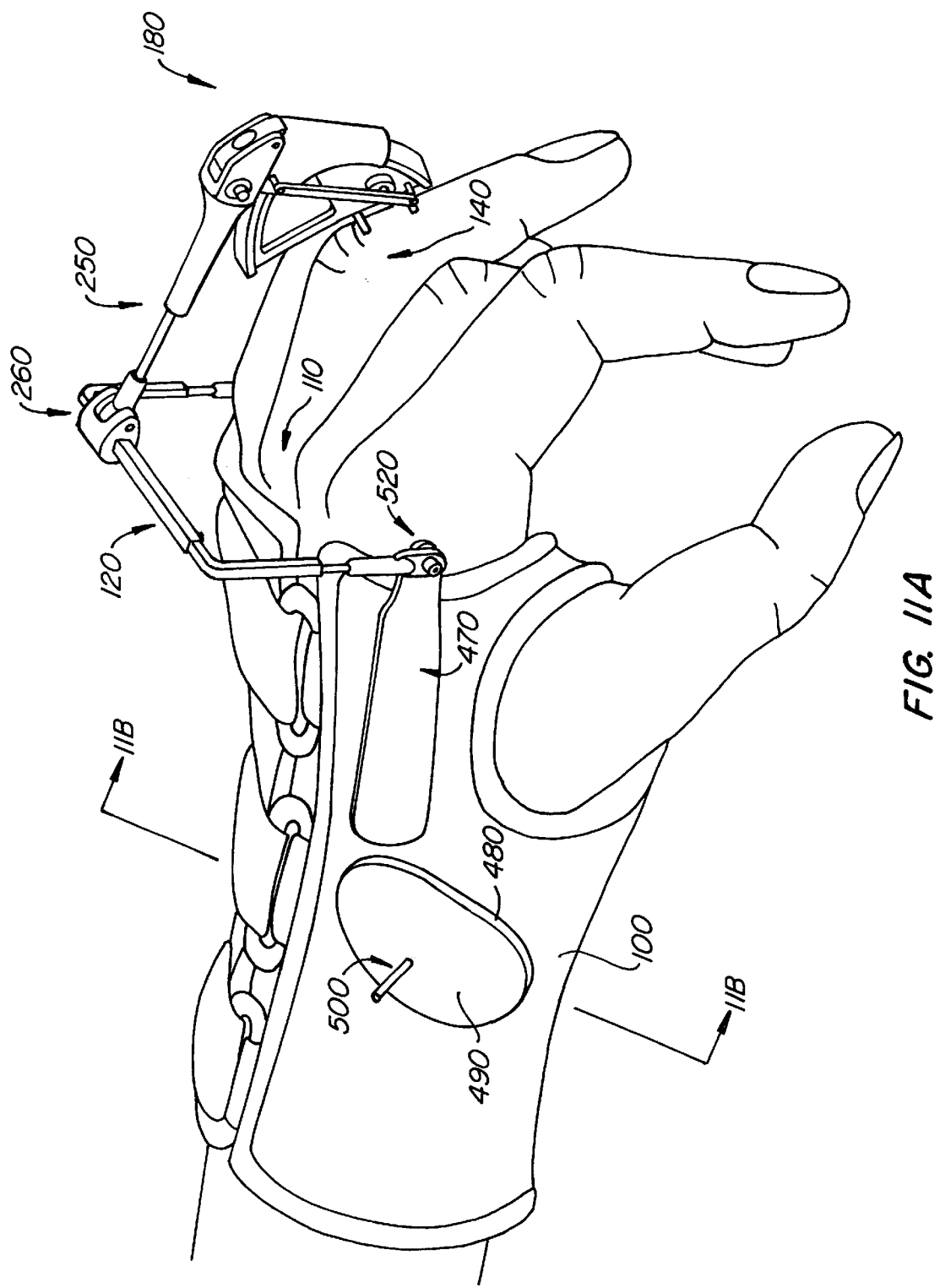
FIGS. 11A and 11B are a perspective view and a cross sectional view, respectively, of a variation of the present invention having a proximal direct skeletal fixation.
Figure 11B:
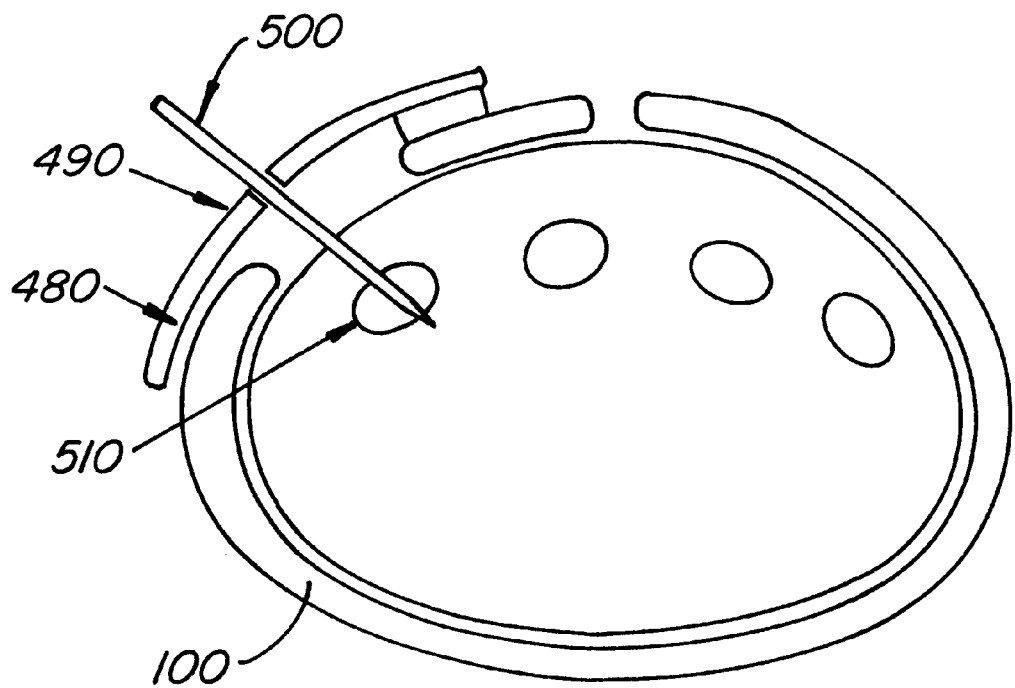

Referring to FIGS. 1A and 1B, perspective and cross sectional views, respectively, are depicted of a variation having a wrist brace 100 which is stabilized upon the wrist by a skeletally-affixed elongate element 500, preferably a K-wire or bone screw. As shown in FIG. 11A, a mechanical assist joint 180 is configured to bias a PIP joint 140. The mechanical assist joint 180 is coupled to a "U" shaped transverse structural member 120 using a rigid linkage 250. The "U" shaped transverse structural member 120 is rotatably coupled to the brace 100 with coupling plates 470 using ball and socket joints 520. The elongate element 500 is preferably positioned before the wrist brace 100 has been positioned and therefore a configuration is needed for coupling the wrist brace 100 with the elongate element 500 in a manner in which loads can be effectively transferred. The depicted variation incorporates a load transfer plate 490 which may be removably and perimetrically coupled, preferably using a Velcro coupling 480 (preferably of a "VELCRO"-type material), to the area around the perimeter of a window in the wall of the wrist brace 100 as shown in FIG. 11B. After the elongate member has been affixed to a wrist or hand bone, preferably a metacarpal bone as shown in FIG. 11B, the wrist brace 100 may be placed upon the wrist and firmly fastened with the elongate element 500 projecting out of the wrist brace 100. The load transfer plate 490, configured to have a hole slightly larger than the outer diameter of the elongate element 500, slides along the elongate element 500 and is coupled perimetrically to the wrist brace 100 using the preferred "VELCRO-type" coupling. The close fit between the hole in the load transfer plate 490 and the elongate element 500 ensures that loads may be transferred between these two elements, thus stabilizing the relative positioning between the wrist brace 100 and the bones of the hand and wrist.

Figure 12A:
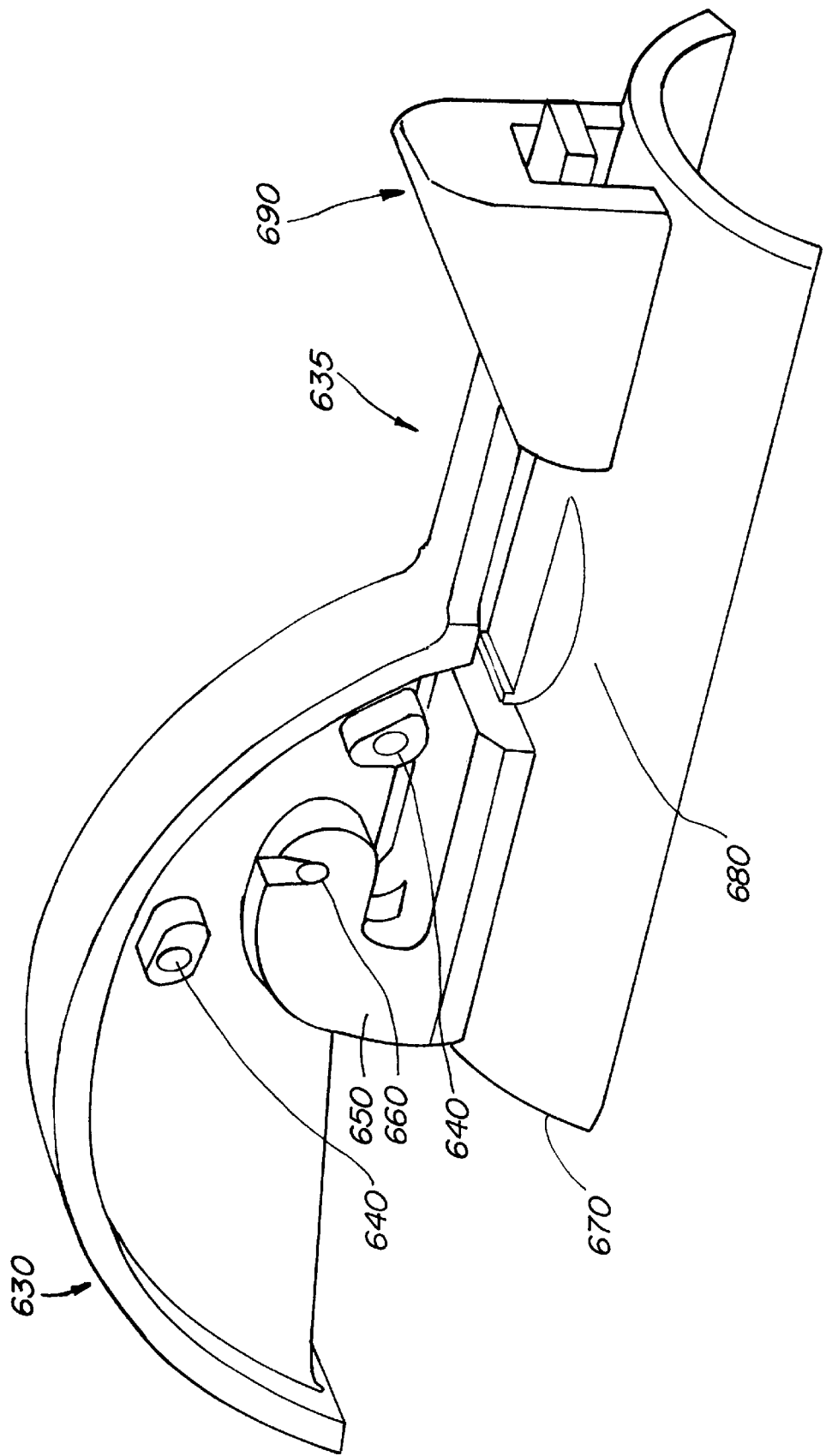
FIG. 12A is a perspective view of a variation of a distal portion of the present invention configured to mount to a finger nonsurgically.

Referring to FIG. 12A, a variation of a distal portion of a joint biasing apparatus is depicted. This portion is particularly configured nonsurgically to attach to a finger in a manner which allows for load application and load bearing while minimizing the embarrassment of the local blood supply of the associated skin, which can lead to discomfort, sores, and other injuries. As shown in FIG. 12A, an arcuate track member 630 similar to those mentioned above is depicted, this variation having an elongate distal extension 635. The arcuate track member 630 is configured to slidably interface with a slider block such as the slider block 190 depicted in FIG. 3. The elongate distal extension 635 is constrained by the distal mounting block 690, which also serves as an angled platform for coupling a finger to the construct using adhesive tape. The arcuate track member 630, preferably constructed from a lightweight metal such as aluminum or a relatively stiff polymer with low friction coefficients which is easily formable and machineable, such as Ultem (RTM) or Delrin (RTM), is coupled to a mounting block 650 of a similar material, using a joint pin 660. As shown in FIG. 12A, pin mounting locations 640 on the arcuate track member 630 are provided for placing a pin to which a tension or extension load element may be coupled. The mounting block 650 and distal mounting block 690 are fastened to a flexible finger contact base 670 having a throughhole 680 preferably using a rubberized adhesive. The flexible finger contact base, preferably comprising a material such as Wonderflex Lined Silicone Gel Sheet from AliMed, Inc, Dedham, Mass., has a large surface area and is capable of spreading loads over the surfaces of a finger without causing potentially injurious load concentrations. A key aspect of this variation of the distal componentry is that the pivot 660 substantially prevents moments from transferring to the base 670, thus preventing stress concentrations at the edges of the base 670 where they contact the skin. In other words, the base 670 is prevented from being placed in bending because the low friction joint pin 660 and mounting block 650 interface substantially prevents the transfer of moments which are substantially coincident with the axis of the joint pin 660. This variation of the distal construct results in distribution of loads across a large surface of the contact base 670 while minimizing undesirable bending-related stress concentrations along the edges of the contact base 670. The mechanical interaction between the distal extension 635 and the distal mounting block 690 results in a slight biasing load of the DIP joint due to the mechanical constraint of the distal extension 635 as its associated arcuate track member rotates in flexion or extension. Therefore the distal mounting block 690 not only serves as a rotational constraint for the associated arcuate track member 630, but also it serves as a potential source of DIP joint biasing in the same rotational direction as the adjacent PIP joint.

Figure 12B:
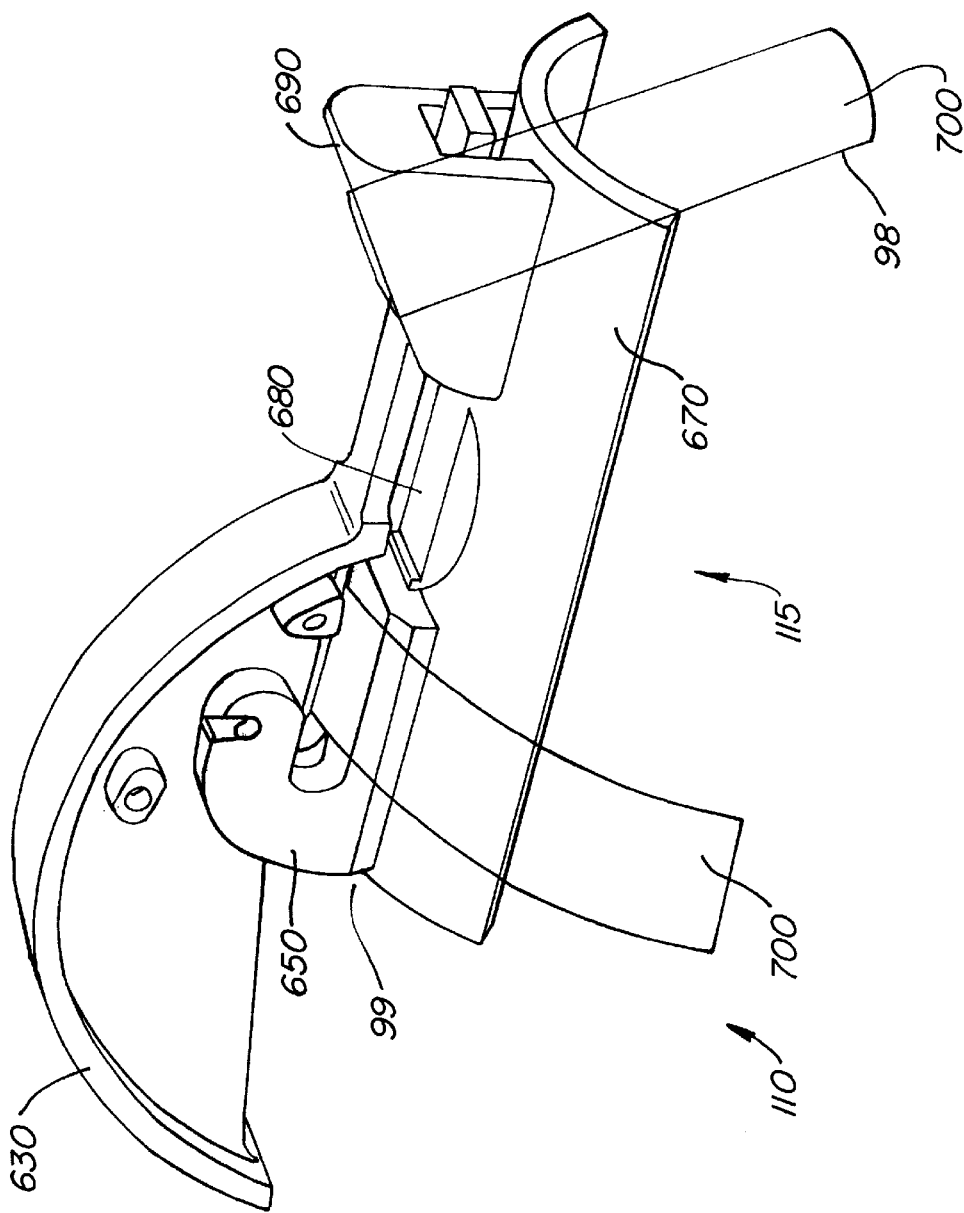
FIG. 12B is a perspective view of the variation depicted in FIG. 12A nonsurgically mounted to a finger.

Referring to FIG. 12B, the variation depicted in FIG. 12A is shown coupled to a finger 99. The finger contact base 670 and other associated components are fastened to the finger 99 using adhesive tape 700 in bands around the mounting block 650 and distal mounting block 690. The distal mounting block 690 provides an angle for placing the adhesive tape 700 at angle around the pulp end 98 of the finger 99, a configuration which is believed to be anatomically favorable for the involved tissues. The depicted configuration, when coupled to a slider block (not shown) along the arcuate track member 630, restricts the range of motion at the DIP joint 115 and biases the PIP joint 110 in accord with any biasing loads applied between the slider block (not shown) and the arcuate track member 630. The throughhole 680 in the finger contact base 670 is configured to allow for limited flexion and extension at the DIP joint, limited, of course, by the interference between the distal extension 635 and the distal mounting block 690.

Figure 13A:
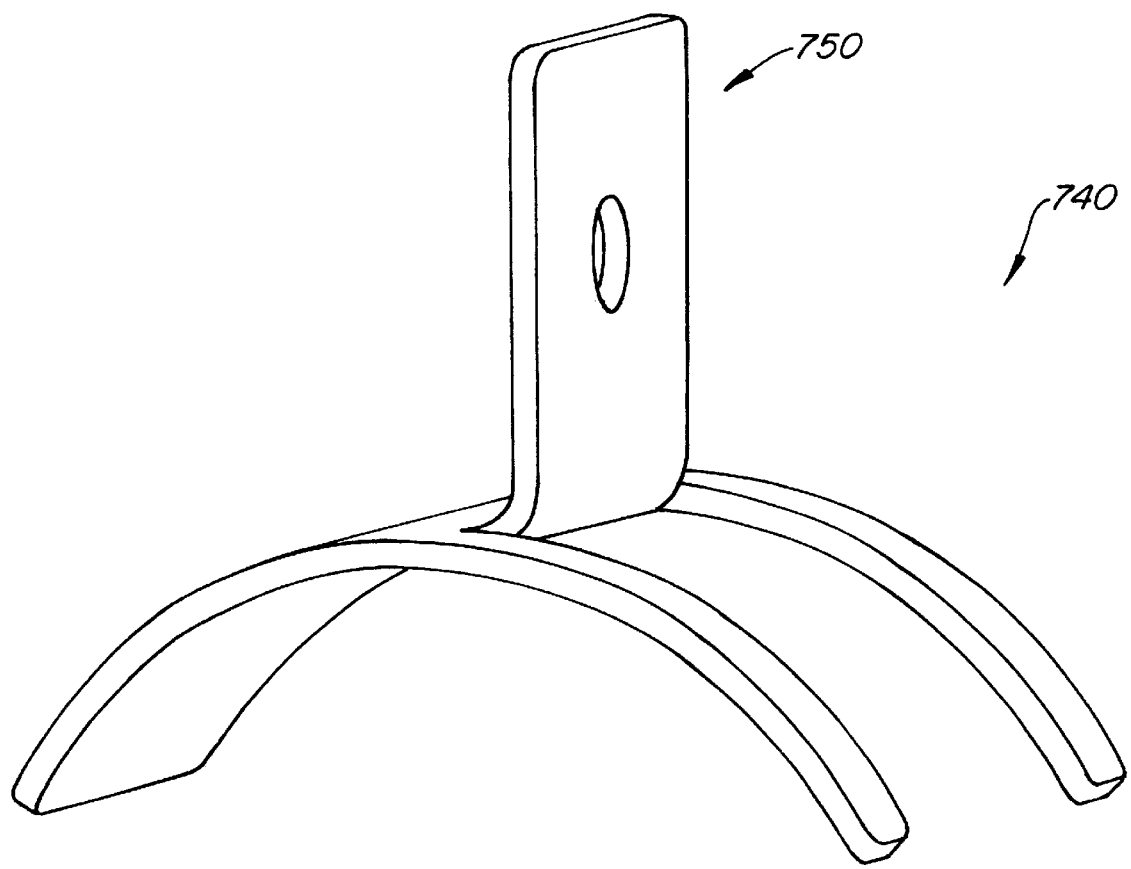
FIG. 13A is a perspective view of a saddle structure portion of a nonsurgically mountable distal portion of a variation of the present invention.
Figure 13B:
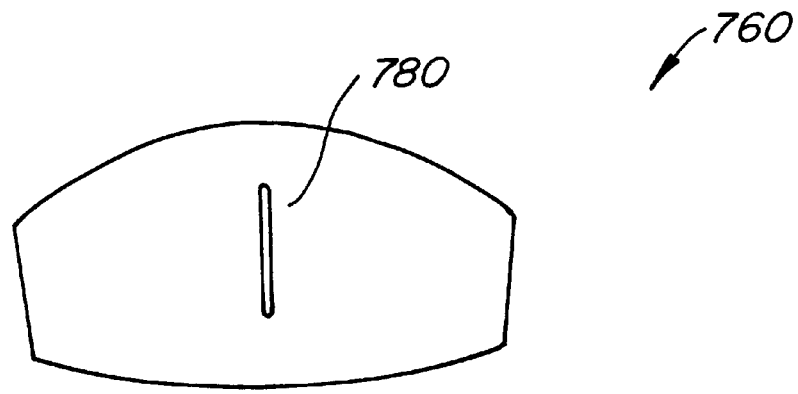
FIG. 13B is a top view of an unassembled wrap member configured to partially form a nonsurgically mountable distal portion of a variation of the present invention.
Figure 13C:
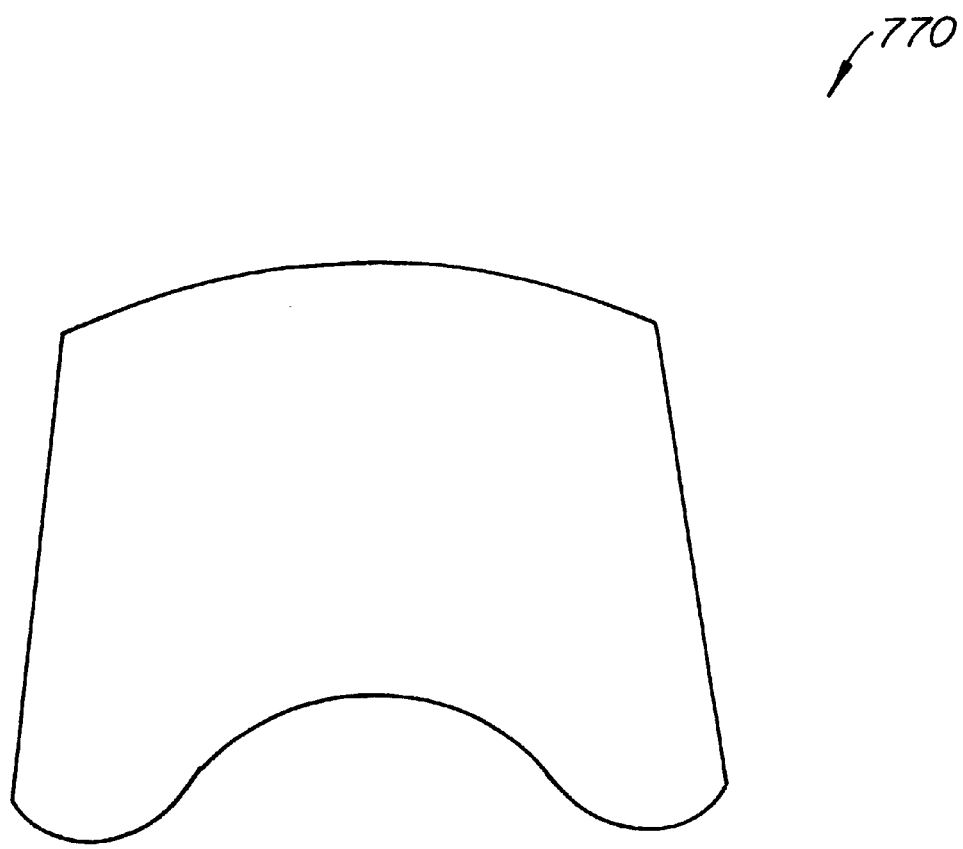
FIG. 13C is a top view of an unassembled wrap member configured to partially form a nonsurgically mountable distal portion of a variation of the present invention.

FIGS. 13A–13G depict another variation of a nonsurgical distal construct which is configured to provide functionality similar to that described above and depicted in FIGS. 12A and 12B. In particular, the variation of FIGS. 13A–13G provides a tower construct to which other components may be attached, the tower being configured to prevent the transfer of moments in a similar manner as the variation described above and in FIGS. 12A–12B. Referring to FIG. 13A, a saddle structure 740 portion of a nonsurgical finger encapsulating construct is depicted having a dorsal hinge tower 750 which rises above the rest of the structure. The saddle structure 740 is preferably constructed from cut, bent, and drilled sheet metal. Referring to FIG. 13B, a dorsal overlying wrap member is depicted having a hole 780 configured to accommodate the dorsal hinge tower 750 of the saddle structure 740. Referring to FIG. 13C, a circumferential underlying wrap member is depicted. Each of the wrap members 760, 770 preferably comprises a formable thermoplastic, such as those commonly used in hand therapy for making braces and other structures. Suitable thermoplastic products include Orfit from North Coast Medical. Such material is generally porous and becomes formable at temperatures slightly above body temperature.

Figure 13D:
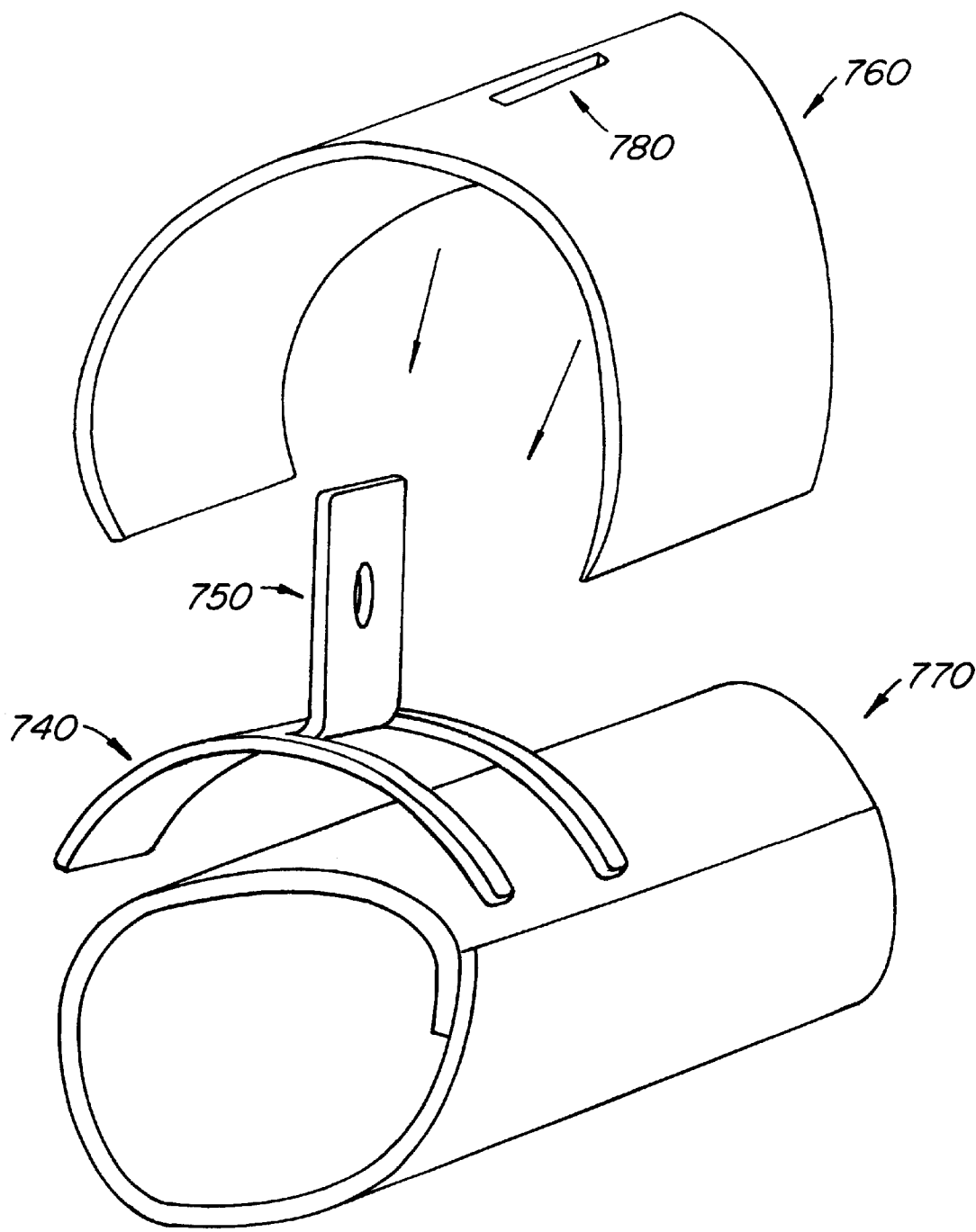
FIG. 13D is a partial assembly view of the structures depicted in FIGS. 13A–13C.

Referring to FIG. 13D, the structures depicted in FIGS. 13A–13C are shown in a rough assembly format. After the circumferential underlying wrap member 770 is wrapped to a comfortable tightness around a finger, the saddle is placed on the dorsal aspect of the finger over the underlying wrap member 770, and is then encapsulated by the dorsal overlying wrap member 760 in a position wherein the dorsal hinge tower 750 extends through the hole 780 in the overlying wrap member 760. The construct is designed to provide a hinge tower 750 to which an acruate track member such as that shown in FIG. 3, and other associated structures may be coupled, the hinge tower being interfaced with the skin of the finger in a manner which distributes loads as much as possible to avoid injuries associated with stress concentrations.

Figure 14:
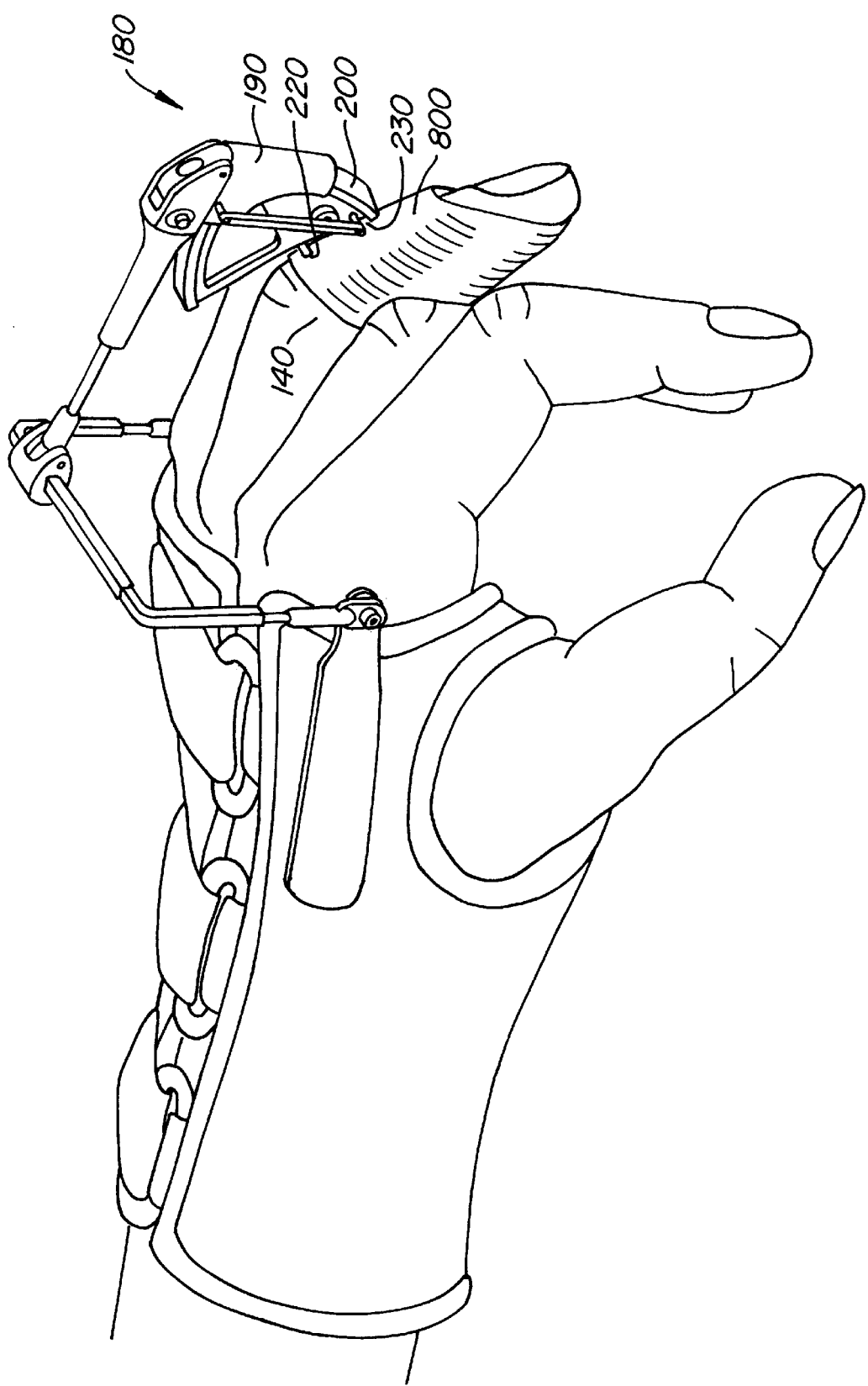
FIG. 14 is a perspective view depicting a variation of the present invention having a nonsurgically mountable distal portion having mounting pins.

Referring to FIG. 14, a variation of the inventive device is shown in perspective view having a distal wrap assembly 800 coupled to the finger. This particular distal wrap assembly, comprising two wrap members similar to those depicted in FIGS. 13B and 13C, uses two metal pins 220, 230 for fixation of other componentry rather than a dorsal hinge tower as in the construct depicted in FIG. 13D.

The foregoing description is considered to be for illustrative purposes only and in no way limiting to the invention. Many other modifications and alterations in the structure and method of operation of this invention will be apparent to those skilled in the art without departing from the scope and spirit of the invention. In particular, the invention can be used with adjacent joints along and appendage other than the example joints pictured. Additionally, other functionally equivalent materials and geometries can be substituted for those components described above.

What is claimed is:

1. An apparatus for biasing a joint of a human upper extremity, the upper extremity having skin, a skeletal structure, and at least one finger with a dorsal aspect and at least one extremity joint, said apparatus comprising:
   a. a distal attachment portion having a distal attachment interface;
   b. a frame;
   c. a proximal attachment portion; and
   d. a first biasing member configured to apply a first moment between said frame and said distal attachment portion about a first moment axis;
   wherein said distal attachment portion is configured to affix to a distal attachment site on the dorsal aspect of a finger at said distal attachment interface, said proximal attachment portion is configured to attach to a portion of the extremity proximal to the distal attachment site, and said frame is rotatable with respect to both said distal attachment portion and said proximal attachment portion; and
   wherein said frame is configured removably to attach to up to four distal attachment portions, each of the up to four distal attachment portions being attachable to one of up to four different fingers of the same extremity.

2. The apparatus of claim 1, further comprising a proximal biasing member, said proximal biasing member being removably attached to both of said frame and said proximal attachment portion and being capable of applying a proximal biasing moment therebetween, said proximal biasing moment being operational to rotationally bias each of said up to four fingers which has a distal attachment portion attached thereto, and to bias them together in the same rotational direction.

3. A method of using the apparatus of claim 2 to bias joints of up to four different fingers of the human upper extremity in the same direction comprising affixing up to four distal attachment portions to the dorsal aspects of said up to four different fingers, removably attaching a proximal biasing member between said frame and said proximal attachment portion, and applying a moment between said proximal biasing member and said frame.

4. The apparatus of claim 2, wherein said proximal biasing moment is applied about an axis of rotation, said axis of rotation being substantially coincident with the axes of rotation of the metacarpophalangeal joints of said extremity.

5. The apparatus of claim 1, wherein said frame is simultaneously rotatable with respect to up to four distal attachment portions and removably attached to up to four biasing members, wherein each of the up to four distal attachment portions is attachable to one of up to four different fingers, each of said, up to four different fingers being of the same extremity, and wherein a different biasing member is removably attachable to said frame and with each of the up to four distal attachment portions thus producing up to four distal biasing moments between said frame and each of the up to four distal attachment portions, said apparatus being capable of independently biasing each of the up to four distal attachment portions with the up to four biasing moments.

6. The apparatus of claim 5, wherein each of said up to four biasing members may be configured to apply a flexion moment or an extension moment.

7. The apparatus of claim 5, wherein the up to four distal attachment portions are attached to up to four different fingers at up to four distal attachment sites, each of said up to four distal attachment sites being on the dorsal aspect of the middle phalanx of up to four different fingers.

8. The apparatus of claim 5, further comprising a proximal biasing member, said proximal biasing member being removably attached to both of said frame and said proximal attachment portion and being capable of applying a proximal biasing moment therebetween, said frame being capable of applying said proximal biasing moment independently from the up to four biasing moments, said proximal biasing moment being operational to rotationally bias each of said up to four fingers which has a distal attachment portion attached thereto, and to bias said up to four fingers together in the same rotational direction about a proximal biasing axis of rotation.

9. The apparatus of claim 8, wherein each of said up to four biasing members is configured to apply a flexion moment or an extension moment, and wherein said proximal biasing member is configured to apply a flexion moment or an extension moment between said frame and said proximal attachment portion.

10. The apparatus of claim 9, wherein the up to four distal attachment portions are attached to up to four different fingers at up to four distal attachment sites, each of said up to four distal attachment sites being on the dorsal aspect of the middle phalanx of up to four different fingers, wherein each of up to four proximal interphalangeal joints is urgeable, independently, into either flexion or extension, and wherein each of up to four metacarpophalangeal joints is urgeable, together, into either flexion or extension about said proximal biasing axis of rotation, said proximal biasing axis of rotation being substantially coincident with the axis of rotation of said up to four metacarpophalangeal joints.

11. A method of using the apparatus of claim 8 to independently bias multiple joints of the human upper extremity comprising affixing up to four distal attachment portions to the dorsal aspects of said up to four different fingers, removably attaching each of said up to four biasing members between said frame and one of said up to four distal attachment portions, independently applying up to four biasing moments between said frame and said up to four distal attachment portions, removably attaching a proximal biasing member between said frame and said proximal attachment portion, and applying a proximal biasing moment between said proximal biasing member and said frame independently from the application of said up to four biasing moments.

12. A method of using the apparatus of claim 5 to independently bias up to four joints of the human upper extremity comprising affixing up to four distal attachment portions to the dorsal aspects of said up to four different fingers, removably attaching each of said up to four biasing members between said frame and one of said up to four distal attachment portions, and independently applying up to four biasing moments between said frame and said up to four distal attachment portions.

13. An apparatus for biasing a joint of a human upper extremity, the upper extremity having skin, a skeletal structure, and at least one finger with a dorsal aspect, an MP joint, and a PIP joint, comprising:
   a. a distal attachment portion having a distal attachment interface;
   b. a frame; and
   c. a proximal attachment portion having a proximal attachment interface;
   wherein said distal attachment portion is configured to attach to a finger with said distal attachment interface at a distal attachment site on said finger which is distal of the PIP joint of said finger, said proximal attachment portion is configured to attach to a portion of the extremity proximal to the center of rotation of the MP joint with said proximal attachment interface, and said frame is rotatable with respect to both said distal attachment portion and said proximal attachment portion; and
   wherein said apparatus is configured to avoid direct loading of said finger at locations between said MP joint and said PIP joint of said finger.

14. An apparatus for applying one or more biasing moments to one or more of an MP joint, a PIP joint, and a DIP joint of a finger, said apparatus comprising a frame comprising
   a distal attachment portion distally attachable to said finger at a site which is distal to said PIP joint and configured to transfer loads to said finger at said site distal to said PIP joint, and
   a proximal attachment portion proximally attachable to an extremity portion at or proximal to said MP joint and configured to transfer loads to the extremity portion at or proximal to said MP joint,
   said distal and said proximal attachment portions each being rotatable in relation to other portions of said frame and adapted to apply biasing moments to joints of said extremity,
wherein said apparatus is configured to avoid direct loading of said finger at locations between said MP joint and said PIP joint.

15. The apparatus of claim 14 wherein said proximal attachment portion comprises a brace.

16. The apparatus of claim 15 wherein said brace comprises a skeletal attachment pin, said pin being configured to provide a structural attachment between said brace and a bone of the hand.

17. The apparatus of claim 16 wherein said skeletal attachment pin has a distal end and a proximal end, said distal end being configured to attach to a metacarpal bone, and said proximal end being configured to slidably interface with a load transfer plate, said load transfer plate being attachable to said brace and being configured to circumferentially constrain said distal end of said skeletal attachment pin to prevent relative motion between the metacarpal bone and said brace.

18. The apparatus of claim 14 wherein said proximal attachment portion comprises at least one skeletal fixation pin and is configured to be fixedly attached to a bone of a hand without the use of a brace.

19. The apparatus of claim 18 wherein said proximal portion comprises a coupling plate, said coupling plate having a rotatable interface with said frame and a removably fixed interface with said at least one skeletal fixation pin, said at least one skeletal fixation pin having a distal end configured to fixedly attach to a bone of the hand and a proximal end configured for removable fixation to said coupling plate.

20. The apparatus of claim 19 wherein said rotatable interface between said frame and said coupling plate has an axis of rotation which is substantially coincident with the physiologic axis of rotation of said MP joint.

21. The apparatus of claim 14 wherein said distal attachment portion comprises a first wrap member adapted to partially encapsulate a portion of said finger and configured to distribute loads to a relatively large surface are of the skin of said finger.

22. The apparatus of claim 21 wherein said first wrap member comprises at least one layer of thermoplastic.

23. The apparatus of claim 21 further comprising a second wrap member adapted to partially encapsulate both a portion of said finger and a portion of said first wrap member, thereby forming a wrap construct.

24. The apparatus of claim 23, wherein said wrap construct further comprising a saddle structure partially encapsulated by said first wrap member and said second wrap member and configured to provide structure to said wrap construct.

25. The apparatus of claim 14 wherein said distal attachment portion comprises a mounting block configured for nonsurgical attachment to said finger in a manner which distributes loads to a relatively large surface area of the skin of said finger, and wherein said mounting block is rotatably coupled with said frame.

26. The apparatus of claim 25 wherein an arcuate track member is configured to rotatably couple said frame with said mounting block.

27. The apparatus of claim 26 further comprising a flexible finger contact base fixedly attached to said mounting block and configured to distribute loads noninjuriously to the skin, said flexible finger contact base having a skin contact surface area which is greater than that of said mounting block.

28. The apparatus of claim 27 further comprising a distal mounting block fixedly attached to said flexible finger contact base and configured to interface with said arcuate track member in a manner which limits the rotational motion of said arcuate track member relative to the finger.

29. The apparatus of claim 28 wherein said flexible finger contact base is configured to interface along the dorsal side of a finger from the PIP joint of the finger to the end of the finger, wherein said mounting block is configured to reside in a longitudinal position between the axis of rotation of the PIP joint of the finger and the DIP joint of the finger, said distal mounting block is configured to reside in a longitudinal position between the axis of rotation of the DIP joint and the end of the finger.

30. The apparatus of claim 25 wherein said mounting block and said frame are coupled with a mechanical joint having a mechanical joint axis, said mechanical joint being configured to substantially prevent the transfer of moments substantially aligned about the mechanical joint axis between said mounting block and said frame.

31. The apparatus of claim 30 wherein said mechanical joint is a pinned joint.

32. The apparatus of claim 14 wherein said frame comprises a distal slider block, a middle structural member, and a proximal U-shaped member wherein said distal slider block is configured to rotatably and slidably interface with an arcuate track member portion of said distal portion, wherein said middle structural member is configured to couple said distal slider block to said proximal U-shaped member, and wherein said proximal U-shaped member is configured to couple said middle structural member with said proximal portion.

33. The apparatus of claim 14 wherein said frame comprises a U-shaped member and a structural member, a. wherein said U-shaped member is configured to rotatably attach to said proximal attachment portion and rotate about an axis of rotation substantially coincident with the axis of rotation of the MP joint of the finger;

b. wherein said structural member is configured to be coupled with said distal attachment portion and be rotationally constrained via contact with a portion of said U-shaped member.

34. The apparatus of claim 33 wherein said U-shaped member comprises a slotted U-shaped member.

35. The apparatus of claim 14 wherein said frame comprises a flexible tension element and a structural member, a. wherein said flexible tension element is configured to rotatably attach to said proximal attachment portion and rotate about an axis of rotation substantially coincident with the axis of rotation of the MP joint of the finger; and b. wherein said structural member is configured to be coupled with said distal attachment portion and be rotationally constrained via contact with a portion of said flexible tension element.

36. The apparatus of claim 14 further comprising a first biasing member contacting said frame and said distal portion and applying a first biasing moment about an axis substantially coincident with the physiological rotation axis of the finger joint adjacent to said distal portion as said joint is being rotated through a range of motion.

37. The apparatus of claim 36 wherein said first biasing moment is applied about an axis substantially coincident with the physiological flexion/extension rotation axis of the PIP joint of the finger.

38. The apparatus of claim 36 further comprising a second biasing member contacting said frame and said proximal portion and applying a second biasing moment about an axis substantially coincident with the physiological rotation axis of the MP joint adjacent said proximal portion.

39. The apparatus of claim 38 wherein said first biasing moment and said second biasing moment are applied in a manner in which the associated joints are biased independently.

40. The apparatus of claim 14 further comprising a first biasing member contacting said frame and said proximal portion and applying a first biasing member about an axis substantially coincident with the physiological rotation axis of the MP joint adjacent said proximal portion.

41. The apparatus of claim 40 wherein said first biasing moment only substantially biases joints immediately adjacent the proximal portion.

42. The apparatus of claim 14 wherein said distal attachment portion and said frame are rotatably coupled with a joint, the joint having a joint axis of rotation and being configured to minimize transmission of a moment having a moment axis substantially coincident with the joint axis of rotation across said joint.

43. The apparatus of claim 42 further comprising a first biasing member contacting said frame and said distal portion and applying a load therebetween configured to bias the finger joint proximally adjacent to said distal portion into rotation.

44. The apparatus of claim 14 wherein a first biasing moment may be applied to the finger about an axis substantially coincident with the physiologic flexion/extension axis of rotation of the PIP joint, and wherein a second biasing moment may be simultaneously applied about an axis substantially coincident with the physiologic flexion/extension axis of rotation of the MP joint of the same finger.

45. The apparatus of claim 44 wherein said first biasing moment and said second biasing moment may be applied independently of each other.

46. The apparatus of claim 45 wherein said first biasing moment urges said PIP joint into extension, and wherein said second biasing moment urges said MP joint into extension.

47. The apparatus of claim 45 wherein said first biasing moment urges said PIP joint into extension, and wherein said second biasing moment urges said MP joint into flexion.

48. The apparatus of claim 44 wherein said first biasing moment is produced using a first load element configured to apply a first biasing load between said apparatus and said finger at a site which is distal to the PIP joint of the finger, and wherein said second biasing moment is produced using a second load element configured to apply a second biasing load between said apparatus and said extremity at a site which is proximal to the MP joint of the finger.

* * * * *

UNITED STATES PATENT AND TRADEMARK OFFICE
CERTIFICATE OF CORRECTION

PATENT NO.      : 6,565,563 B1
DATED           : May 20, 2003
INVENTOR(S)     : John M. Agee et al.

It is certified that error appears in the above-identified patent and that said Letters Patent is hereby corrected as shown below:

<u>Title page,</u>
Item [73], Assignee, should read -- John M. Agee, Sacramento, Calif.; Trustee of John M. Agee Trust dated August 15, 1996 --

Signed and Sealed this

Fourteenth Day of October, 2003

JAMES E. ROGAN
*Director of the United States Patent and Trademark Office*